US006406850B2

(12) United States Patent
Volkers et al.

(10) Patent No.: US 6,406,850 B2
(45) Date of Patent: Jun. 18, 2002

(54) APPLICATIONS WITH AND METHODS FOR PRODUCING SELECTED INTERSTRAND CROSS-LINKS IN NUCLEIC ACIDS

(75) Inventors: Herman Volkers, Monnickendam; Robert Heetebrij, Leiden; Hendrik-Jan Houthoff, Amsterdam; R. P. M. van Gijlswijk, Alphen aan de Rijn; Hendrikus Johannes Tanke, Rijnsburg; Anton Klaas Raap, Leiden, all of (NL)

(73) Assignee: Kreatech Biotechnology B.V., Amsterdam (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/454,404

(22) Filed: Dec. 3, 1999

(30) Foreign Application Priority Data

Dec. 3, 1998 (EP) .............................................. 98204094

(51) Int. Cl.⁷ ........................... C12Q 1/68; C12P 19/34; C07H 21/04; C07H 21/02
(52) U.S. Cl. ........................... 435/6; 435/91.2; 436/536; 536/24.3; 536/24.32; 536/24; 536/26.7; 536/26.8
(58) Field of Search ...................... 435/6, 91.2; 536/24, 536/26.6, 24.32, 26.7, 26.8; 436/536

(56) References Cited

U.S. PATENT DOCUMENTS

| 5,476,928 A | * 12/1995 | Ward et al. .................... 536/24 |
| 5,538,869 A | * 7/1996 | Sicilliano et al. .......... 435/91.2 |
| 5,589,339 A | 12/1996 | Hampson et al. ............... 435/6 |
| 5,591,575 A | * 1/1997 | Hampson et al. ............... 435/6 |
| 5,652,096 A | 7/1997 | Cimino .......................... 435/6 |
| 5,831,073 A | 11/1998 | Rokita et al. ............... 536/26.6 |
| 5,859,259 A | * 1/1999 | Sinha et al. ............. 548/303.7 |

FOREIGN PATENT DOCUMENTS

| FR | 2 755 146 A1 | 4/1996 |
| FR | 2755146 A1 | 10/1996 |
| WO | 90/14353 | 11/1990 |
| WO | 96/20289 | 7/1996 |
| WO | 98/15565 | 4/1998 |

OTHER PUBLICATIONS

Speicher et al., "Karyotyping human chromosomes by combinatorial multi-fluor FISH", *Nature Genetics*, vol. 12, pp. 368–375, Apr. 1996.*

Bernal–Mendez et al., "Chemical versatility of transplatin monofunctional adducts within multiple site–specificity platinated DNA", *Biochemistry*, vol. 36 (24), pp. 7281–7287, Jun. 1997.*

Craig, Jeffrey M., et al. "Removal of Repetitive Sequences from FISH Probes Using PCR–assisted Affinity Chromatography", Hum. Genet. 100 (1997) 472–476 (Sep. 1997).

* cited by examiner

*Primary Examiner*—Jeffrey Fredman
*Assistant Examiner*—Arun K. Chakrabarti
(74) *Attorney, Agent, or Firm*—Hoffman & Baron, LLP

(57) ABSTRACT

The Invention relates to a method for providing at least one selected sequence in a nucleic acid with interstrand cross-links. The method comprises hybridizing at least one selected single strand sequence with a complementary single strand nucleic acid or a functional analogue thereof. The selected sequence or complementary nucleic acid or both comprise a cross-linking agent. The invention also relates to a method, referred to as COBRA, for the labeling of a set of at least two bio-organic molecules with a set of at least two colors, comprising generating said set of colors through combining ratio labeling with binary labeling.

39 Claims, 10 Drawing Sheets

APPLICATIONS WITH AND METHODS FOR PRODUCING SELECTED INTERSTRAND CROSS-LINKS IN NUCLEIC ACIDS

FIELD OF THE INVENTION

The invention lies in the field of nucleic acid cross-linking and uses thereof. More specifically the invention relates to methods for producing selected interstrand cross-links in nucleic acids and uses thereof. One important aspect of the invention relates to the use of selected interstrand cross-links for the selective amplification of certain nucleic acids in an amplification reaction.

BACKGROUND OF THE INVENTION

Many different compounds have been identified that posess nucleic acid cross-linking activity. Cross-linking of nucleic acids is most commonly used for therapeutic purposes in the intervention with proliferative disorders such as cancer. Most cross-linking agents cross-link nucleic acids in very specific ways and on specific places in nucleic acids. However, the frequency of these specific places in most nucleic acids are so high that effectively the cross-links are provided throughout the nucleic acid molecules. For the use of these cross-linking compounds in the intervention of cancer this so-called apparently random cross-linking activity does not prevent some kind of a therapeutic effect. However, in the ideal situation cross-links would only be applied in the nucleic acid of the cells of which the proliferation should be interfered with. For instance by applying the cross-links only to those nucleic acids involved in the transformation of said cell, i.e. the oncogenes or the RNA of said oncogenes. Such specificity was not possible with the current methods of cross-linking. The apparent random cross-linking activity of cross-linking agents also prevents the use of these compounds in assays that require more specific cross-linking. In one aspect the invention provides a method for producing cross-links in selected regions of a nucleic acid. In one aspect said method may be used to prevent at least in part, certain regions in a nucleic acid from taking part in a process such as, but not limited to, a process comprising a hybridisation or an amplification or both. In one aspect said method of producing selected interstrand cross-links is used in a process for producing a probe deprived at least in part of repetitive sequences. Such a probe is useful for the detection of for example nucleic acid sequences in chromosome painting in the field of cytogenetics.

The introduction of fluorescence in situ hybridisation (FISH) has significantly changed cytogenetics. Human FISH karyotyping is now successfully applied to elucidate complex chromosome rearrangements. Multi-colour FISH analysis of chromosomes is not necessarily restricted to the use of whole chromosome paints. Recently, sets of probes have been generated that specifically recognise the (sub) telomeric regions of a particular chromosome and that are applied in a multi-colour FISH format to detect cryptic translocations, frequently occurring in mental retardations. The selective staining of 24 human chromosomes is at present accomplished through binary combinations of probes that are labelled with 5 distinct fluorophores (Schroeck et al., 1996; Speicher et al., 1996).

For this so-called combinatorial labelling [also called multiplex FISH] the number of recognisable targets (n) using (k) different fluorophores is $n=2_k-1$ colours. Five fluorophores thus allow a maximum of 31 colours, sufficient to recognise 24 chromosomes, but insufficient for instance to explore the use of p and q arm specific probes for the detection of intrachromosomal rearrangements. Thus, multi-colour FISH analysis of chromosomes would benefit directly from a method to increase the number of simultaneously recognisable targets beyond the 27 reported so far (Nederlof et al., 1992; Dauwerse et al., 1992; Morrison and Legator, 1997). Higher FISH multiplicity is achievable by ratio labelling. This technique, by which a given probe is composed of a mixture of probes with different fluorescent labels, has great potential. As an illustration, one may consider the number of recognisable colours that could be composed with the three primary colours blue, green and red. In practice though, ratio labelling is considerably more complex than combinatorial labelling. Recognition of chromosomes stained with ratio labelled probes is not a "yes or no colour" decision (as in the binary approach) but requires accurate measurement of colour.

SUMMARY OF THE INVENTION

The present invention provides methods for the selected cross-linking of nucleic acids. Specific regions in nucleic acids can be selected and specifically cross-linked with minor or not detectable "a-specific" cross-linking in not selected regions. The method is used in one non-limiting application, for the selected amplification of certain sequences from a pool of potentially amplifiable sequences. The method is used in another non-limiting application for the preparation of a probe for the detection of nucleic acids wherein selected sequences are at least in part prevented from taking part in a hybridisation reaction. In one aspect the invention provides a method for the generation of a probe for the detection of chromosomes or parts thereof. In one non-limiting example of such a probe said probe is labelled by means of one aspect of the COBRA technique of the invention.

DETAILED DESCRIPTION OF THE INVENTION

In one embodiment, the invention provides a process for producing selected interstrand cross-links in nucleic acids comprising hybridising single strand nucleic acid(s) with complementary single strand nucleic acid(s) or a functional analogue thereof, wherein said nucleic acid(s) or said complementary nucleic acid(s) or both comprise a cross-linking agent. In a preferred embodiment of the invention only said single stranded nucleic acid(s) or said complementary nucleic acid(s) comprises a cross-linking agent. Said nucleic acid, preferably said complementary nucleic acid, may also be a functional analogue of a nucleic acid. One such analogue comprises peptide nucleic acid (PNA). In a preferred embodiment of the invention said nucleic acid or said complementary nucleic acid or both are DNA. A preferred principle for selecting a nucleic acid region is through hybridisation with one or more nucleic acids complementary to said region. Cross-links may be provided through a cross-linking agent. Cross-links may be provided by hybridising one or more complementary nucleic acids to a nucleic acid thereby selecting regions for cross-linking, and contacting said nucleic acid with a cross-linking agent. The selected double stranded regions are cross-linked whereas the non-selected single stranded regions are not cross-linked. For some purposes excess cross-linking agent and/or cross-linking agent (or reaction intermediates) not contributing to double stranded intermediates can be removed or inactivated before use of the selectively cross-linked nucleic acid.

Preferably, cross-linking agents are used that cross-link double stranded nucleic acids and that have minor or undetectable cross-linking activity in single stranded nucleic acids. Alternatively, cross-linking agent is linked to the one or more complementary nucleic acids before hybridisation whereupon cross-linking of selected regions is achieved after hybridisation of said complementary nucleic acid to the selected region. Preferably, cross-linking activity of the cross-linking agent is low when the nucleic acid is a single strand form and high when the nucleic acid is in a double stranded form.

Regions in a nucleic acid may be selected for cross-linking by adding complementary nucleic acid to the single stranded form of said nucleic acid and performing a hybridisation. However, advantage may be taken of complementary regions in a nucleic acid in that said complementary regions are induced to hybridise to each other after said nucleic acid has been made single strand and allowed to hybridise. Particularly in this case, but not limited to this case, selection of different regions can be varied by varying the hybridisation conditions. Regions may also be selected for cross-linking by using a combination of the methods mentioned above. For instance some regions may be selected through the addition of complementary nucleic acid(s), whereas other and or the same regions may be selected through hybridisation of complementary regions within a nucleic acid.

It is of course essential that complementary nucleic acids comprises sequences that are complementary to a selected region in a nucleic acid. However, it is not necessary that all sequences in the complementary nucleic acids are in fact complementary to a selected region in a nucleic acid. Extra sequences in said complementary nucleic acids may be useful for a specific purpose or may just be present for convenience as long as they do not prevent the primary function of said complementary nucleic acids, i.e. hybridising to a selected region.

The level of cross-linking and the nature of the cross-link determine tightness of the cross-linking between the selected nucleic acid region and the complementary nucleic acid. The required tightness of the cross-linking varies with the specific application of the invention. In applications wherein selected cross-linking is performed to prevent denaturation of a selectively cross-linked double stranded nucleic acid, the tightness of the linking should be sufficiently high to at least in part prevent denaturation in conditions that would enable denaturation of the selected region without cross-linking.

In one embodiment of the invention the cross-linking agent comprises a transition metal, preferably platinum, capable of cross-linking double stranded nucleic acids. In a preferred aspect of this embodiment the cross-linking agent comprises (trans)-dichlorodiam(m)ineplatinum.

Trans-dichlorodiammineplatinum (II) (trans-DDP) can form intrastrand cross-links between adjacent base residues in a DNA strand (Cohen et al., 1980). The intrastrand cross-links between two guanine (G) residues, or between a G and a cytosine (C) residue, or between a G and a cytosine (C) residue separated by at least one residue, are the most favourable ones (Eastman et al., 1988; Pinto et al., 1985; Lepre et al, 1987). The 1,3-intrastrand cross-links between trans-DDP and two G residues separated by one intermediate base are stable within single-stranded oligonucleotides. As soon as the platinated oligonucleotides hybridise to their complementary strands the 1,3-intrastrand cross-links rearranges to form an interstrand cross-link (Dalbies et al., 1994). This interstrand cross-linking effect of trans-DDP can be used in a strategy to selectively cross-link certain nucleic acid sequences in a pool of nucleic acid sequences.

In one application of the invention selected interstrand cross-links are provided in oncogenes present in the DNA of cells that are transformed or in the process of transforming. In this application said interstrand cross-links are provided to hamper at least in part replication and/or transcription of said oncogenes. Said application may be useful in the treatment or prevention of cancer.

In another application of the invention is provided a method for the selected interstrand cross-linking of selected sequences in a nucleic acid sequence comprising hybridising at least one selected single strand sequence with a complementary single strand nucleic acid wherein said selected sequence or said complementary nucleic acid or both comprise a cross-linking agent, wherein said cross-linking hampers further hybridisation and/or replication of said selected sequence. In another application of the invention repetitive sequences in a nucleic acid are selectively cross-linked to block the amplification of the selected region(s).

For chromosome painting, chromosome-specific DNA is used as a probe. This probe is generally obtained by performing a PCR based amplification, such as but not-limited to DOP-PCR, on DNA of specific chromosome, which is isolated by flow sorting or micro-sectioning. Chromosomal DNA contains a lot of repetitive sequences, like telomeric DNA, centromeric repeats, LINEs, SINEs and VNTRs. During DOP-PCR, these repetitive sequences will also be amplified and in in situ hybridisation experiments, they will create differential labelling of all chromosomes. Normally this background labelling is prevented by adding repetitive DNA to the hybridisation mixture, which consists of a pool of repetitive sequences. However, the technique of using repetitive DNA for this purpose is not ideal because the background is not reduced completely and also the signal of the probe is reduced.

In order to circumvent the necessity of blocking during hybridisation it would be desirable to exclude the presence of repetitive sequences in the probe DNA. Methods to remove repetitive sequences by subtraction are known in the art (Craig et al., 1997). Subtraction methods are not preferred because they require additional manipulation of the probe and subtraction is not easy to reproduce. The problem with the current methods of producing a probe with a satisfactory low level of repetitive sequences is that during the generation of the probe, repetitive sequences are also generated. Since repetitive sequences are also generated in the probe measures have to be taken to eliminate their hybridisation or to remove them from the probe. These measures have as yet problems as mentioned above. With the methods of the invention we have designed a novel approach to produce a probe, wherein the probe is generated under conditions that prevent or lower the amount of repetitive sequences generated. This procedure results in a probe that has a lower contamination with repetitive sequences which (for most purposes) can be used directly. However, if further removal of repetitive sequences is desired the probe generated through the methods of the invention also presents a better substrate for the subsequent prevention of hybridisation of repetitive sequences strategies or the removal of repetitive sequences from the probe, since the probe already was less contaminated with repetitive sequences to begin with.

The following is a non-limiting example of an aspect of the invention wherein a strategy of designing a probe with a low amount of repetitive sequences is described. DOP-PCR is performed with degenerative primers on chromosomal DNA, isolated by flow sorting or micro-sectioning. During the DOP-PCR the repetitive sequences are being cross-linked by trans-DDP labelled nucleotide sequences, complementary to these sequences, wherein said nucleotide sequences are preferably one or more trans-DDP labelled oligonucleotide sequences.

Hybridisation of the trans-DDP labelled nucleotide sequences to their target results in stable interstrand cross-link of the nucleotide sequences to the selected repetitive regions. These nucleotide sequences may be modified to lack the 3' hydroxy group thus disabling the nucleotide sequences to function as a primer by the polymerase. Therefore amplification will be blocked at the position of the cross-linked nucleotide sequences and preferentially unblocked sequences, which do not contain selected repetitive sequences will be amplified. As a consequence, the amplification product can be used as a probe for chromosome painting experiments directly without adding repetitive nucleic acid(s) to the hybridisation mixture. Alternatively, due to the reduced presence of repetitive sequences significantly less repetitive nucleic acid(s) needs to be added to the hybridisation mixture thereby significantly improving the performance of a probe in the presence of repetitive nucleic acid(s).

Blocking of amplification of specific sequences can also be used in other PCR-applications or in vitro transcription assays. Furthermore in all situations where an increased stability of a connection between a DNA or a RNA-strand and its target is required, selective cross-linking, for instance through trans-DDP, can be applied. In the antisense technique, translation of certain messenger RNAs (MRNA) is prevented by the presence of selectively cross-linked antisense oligonucleotides. Trans-DDP can create a stable connection between these oligo's and the mRNA. In contrast, enhancing translation by stabilising secondary structures of mRNAs is also possible with trans-DDP.

In one aspect of the invention is provided a process for the generation of a probe from which selected sequences, preferably repetitive sequences, are at least partially prevented from functioning as a probe (i.e. a nucleic acid provided with a label used for detection of the presence of said probe) through providing selected regions in a nucleic acid probe with interstrand cross-links. Said probe may be used in applications were nucleic acids probes are used for the detection of the presence of the probe such as but not limited to micro arrays, southern blots, northern blots, chromosome painting, etc. Advantages of a probe from which selected sequences are prevented from functioning of a probe are clear to the person skilled in the art and include but are not limited to improved specificity of said probe.

In one aspect of the invention is provided a process for the selected amplification of certain amplifiable sequences from a pool of amplifiable sequences comprising providing selected interstrand cross-links to decrease, or block at least in part, the amplification of a subset of amplifiable sequences, and subjecting said pool to an amplification reaction.

In a preferred aspect of the invention a pool of amplifiable sequences is selected from sequences present in a chromosome. Preferably a pool of amplifiable sequences is selected from sequences of a part of a chromosome.

A collection of fragments produced during the selected amplification can be used as a probe for the detection of nucleic acid sequences. The probe may be labelled with conventional techniques or the probe may be labelled through the ULS, universal linkage system as described in (WO 92/01699, WO 96/35696, WO 98/15564 and WO 98/45304). When the probe is made from sequences from an entire chromosome, the probe may be used to stain an entire chromosome. Similarly, when the probe is made from sequences from a part of a chromosome, the probe may be used to stain a part of said chromosome. Such labelled chromosomes or parts thereof may be used for the typing of a chromosome and/or a cell or for the identification of a disease.0000

One aspect of the invention provides a special labelling technique of bio-organic molecules, called COBRA (Combined Binary Ratio labelling). COBRA is based on the strategic combination of binary labelling and ratio labelling. In a non limiting application the technique is used to achieve FISH multiplicity of 24, 48, 96 or more based on existing technology and only requires a good digital fluorescence microscope.

In one aspect COBRA utilises combinatorial (i.e. binary) labelling and so-called ratio labelling for increasing the number of identifiable colours for use in detection of nucleic acid in for instance cytogenetics. The COBRA labelling can be used for the labelling and/or detection of bio-organic molecules such as nucleic acid, protein, lipid and/or carbohydrate. A number of spectrally separated fluorophores is used for ratio labelling, in such a way that two fluorophores are used to produce a certain colour. When this is applied for three fluorophores, and each pair of fluorophores results in 5 colours, a total of 12 colours is achieved (lower triangle in FIG. 1). This primary probe set is directly fluorescently labelled using methods such as nick translation, random primed labelling, PCR-labelling, and/or chemical labelling. A second set of 12 probes, recognising different targets is labelled exactly the same, but in addition is given a fluorophore. In one example said fluorophore is a hapten, for instance biotin or digoxigenin. This hapten is developed using avidin or antibodies labelled with a fourth fluorescent label, spectrally well distinguishable from the three primary fluorophores used for ratio labelling. Thus, the set of 12 is multiplied by 2, which results in 24 colours using 4 fluorophores only (two middle triangles in FIG. 1), which is one fluorophore less than reported so far to accomplish staining of the 24 human chromosomes. Extra "free" fluorophores may be used to repeat this process, exploring a second binary label, which again results in a doubling of the number of achievable colours (giving 48 colours) (upper triangles in FIG. 1). Clearly, even stronger increments in number of colours are achievable if more than 12 primary colours are produced in the basic triangle, either by using more than three fluorophores or by distinguishing more ratios.

Mathematically, the total number of achievable COBRA colours can, at least in the case wherein two fluorophores are simultaneously used per target, be described as follows. Assume that n fluorochromes are used for ratio labelling and assume that, as a non-limiting example, only 2 of those fluorochromes are simultaneously used per target, while additionally m fluorochromes can be binary labelled to the same target and r ratios can be resolved for ratio labelling, then the number of different colours that can be distinguished is given by the following formula:

$$\text{No. of colours} = (n + ((r \times n!)/(2 \times (n-2)!))) \times 2^m \quad \text{Formula I}$$

with:
$2 \leq n \leq \infty$,
$0 \leq r \leq \infty$ $0 \leq m \leq \infty$

In one aspect, the invention provides a method for the generation of colours called COBRA, suitable for the labelling of probes, by mixing fluorochromes according to formula I, wherein n is the number of fluorochromes used for ratio labelling while, in this non-limiting example, only 2 of those fluorochromes are simultaneously used per target, m is the number of fluorochromes used to binary label the same target, and r is the number of ratios that can be resolved by ratio labelling.

The person skilled in the art will clearly be able to choose suitable fluorophores for use in COBRA. The person skilled in the art will clearly be able to choose suitable ratios of fluorophores in ratio labelling.

In one embodiment of COBRA, the fluorochromes used for labelling may be selected from the group DEAC, Cy3®, fluorescein, Lissamine™ etc.

As used herein the term transition metal means a metal of group VIII of the periodic chart of the elements. A preferred transition metal for use in a cross-linking agent is platinum. In one aspect the invention provides a method for providing at least one selected sequence in a nucleic acid with interstrand cross-links comprising hybridising at least one selected single strand sequence with a complementary single strand nucleic acid wherein said selected sequence or said complementary nucleic acid or both comprise a cross-linking agent. In a preferred embodiment of the invention said selected interstrand cross-links hamper further hybridisation and/or replication of said selected sequences.

In another aspect the invention provides a method for the generation of a probe wherein at least one selected sequence in said probe is at least in part prevented from functioning as a probe through providing said selected sequence with interstrand cross-links. Preferably said selected sequence comprises at least one repetitive sequence.

In one aspect of the invention is provided a method for the selected amplification of certain amplifiable sequences from a pool of amplifiable sequences comprising producing a selected interstrand cross-linked nucleic acid or probe, wherein said selected interstrand cross-links are provided to decrease the amount of amplification of a subset of amplifiable sequences and subjecting said pool to an amplification reaction. Preferably a single stranded nucleic acid is prevented from taking part in said amplification through disabling the primer extension function of hybridised and cross-linked complementary single nucleic acid, preferably through modification of the 3'-hydroxy group.

Preferably said pool of amplifiable sequences is selected from sequences present in a chromosome.

Following amplification said amplification will lead to a collection of amplified sequences, which among others may, upon labelling, be used as a probe. When such pool of amplifiable sequences is selected from sequences present in a chromosome such a probe may be used in the preparation of a chromosome paint.

In a preferred embodiment of the invention a method referred to as COBRA is used for the labelling of a set of at least two bio-organic molecules with a set of at least two colours, comprising generating said set of colours through combining ratio labelling with binary labelling. In one embodiment of COBRA, at least in the case wherein two fluorophores are simultaneously used per target, the total number of distinguishable colours of said combination can be calculated according to formula I, No. of colours=$(n+((r \times n!)/(2 \times (n \times 2)!))) \times 2^m$ wherein n is the number of fluorophores used for ratio labelling where in a non-limiting example, only 2 of those fluorochromes are simultaneously used per target, m is the number of fluorophores used to binary label the same target, and r is the number of ratios that can be resolved by ratio labelling.

with $2 \leq n \leq \infty$,
$0 \leq r \leq \infty$
$0 \leq m \leq \infty$

In a preferred embodiment of COBRA, at least one of said bio-organic molecules comprises nucleic acid, protein, carbohydrate and/or lipid.

In another aspect of the invention is provided a method for simultaneous identification of sequences of at least one chromosome or part thereof, through the use of at least one probe, preferably prepared according to a method of the invention, wherein said probe is labelled according to a COBRA method for doubling the number of identifiable labels obtainable by ratio labelling, comprising adding to a first set of fluorophores, used for the ratio labelling of a first set of probes, a novel fluorophore and labelling a second set of probes.

In one embodiment of the invention a probe for the improved detection of chromosomes or parts thereof is provided. In another embodiment, the invention provides the use of selected interstrand cross-links for decreasing the amount of amplified product of certain amplifiable sequences.

In another embodiment the invention provides the identification of a disease through the typing of at least one chromosome wherein at least one chromosome is labelled, with at least one probe prepared according to the methods of the invention. In yet another aspect of the invention a kit for the detection of nucleic acid is provided, comprising at least one probe obtainable by methods of the invention.

In yet another aspect the invention provides a kit for performing the methods of the invention comprising at least one probe labelled with a COBRA method.

In yet another aspect the invention provides a kit for generating a probe according to the invention, comprising at least a cross-linking agent, preferably linked to a single stranded nucleic acid.

The invention further provides a kit for the detection of nucleic acid comprising at least a collection of amplified sequences or a probe. The invention further provides a kit for performing the selective cross-linking of nucleic acid wherein said kit comprising at least a cross-linking agent, preferably linked to a single stranded nucleic acid.

The invention also provides a molecule comprising at least two parts, cross-linked with a cross-linking agent, wherein said cross-linking agent comprises a transition metal, preferably platinum, wherein at least two of said parts comprise a protein. Such a molecule is for instance produced with a method wherein a protein is labelled with a ULS comprising a label, wherein said label comprises a protein. Preferably said molecule comprises at least two different proteins.

As used herein the term "interstrand cross-link" refers to a physical link between a cross-linking agent and a double stranded nucleic acid, wherein said physical link decreases the propensity of a double stranded nucleic acid, to denaturate. Preferably but not necessarily an interstrand cross-link physically links the two complementary strands of the double stranded nucleic acid.

As used herein the term "physical link" is a covalent or non-covalent bond.

As used herein a probe is defined as collection of nucleic acid sequences comprising at least two different sequences, preferably labelled with a label facilitating detection of said probe. Said probe may by used directly for the detection of for instance nucleic acid sequences or said probe may be manipulated according to the methods of the invention prior to the detection of for instance nucleic acid sequences.

As used herein the term "complementary" in relation to nucleic acids is used functionally, meaning that the homology of a nucleic acid to a complementary nucleic acid is sufficiently high to allow hybridisation of a complementary nucleic acid to a nucleic acid under the desired stringent or non-stringent hybridisation conditions. This functional definition is necessary to allow for different hybridisation conditions that may be utilised in practising the invention. One non-limiting example that illustrates the necessity for a functional definition is the cross-linking of a specific region which is repeated several times in a nucleic acid but where the repeated regions vary slightly in the exact nucleotide sequence. Choosing a nucleotide sequence which is completely homologous to one region automatically implies that said nucleotide sequence is not completely homologous to the sequences of the repeated regions. The chosen sequence is however functionally homologous to the sequences in the repeated regions, i.e. complementary, when the sequence dissimilarity of said repeated regions does not, under the chosen hybridisation conditions, prevent hybridisation of the chosen sequence with said repeated regions.

EXAMPLES

Example 1

Blocking Hybridisation of Repetitive DNA by Trans-DDP Labelled Repetitive DNA

Two slides with metaphase chromosomes are hybridised with Cy3-ULS labelled repetitive DNA. The first slide is prehybridised with unlabelled repetitive DNA. The second slide is prehybridised with trans-DDP labelled repetitive DNA.

Since hybridisation of trans-DDP labelled repetitive DNA to its target will create a stable interstrand connection, hybridisation of Cy3-ULS labelled DNA is prevented on the second slide. Therefore the Cy3 signal on the chromosomes is much lower on the second slide than on the first slide (see table 1 for details).

Slides 1, 2 and 3 are control slides. The numbers of 1:0 represent the amount of repetitive DNA in relation to the amount of trans-DDP. For the slides 2 and 3, no trans-DDP was used and there was no cross-linking. The acquired results thus have to be seen as reference values. The results of slides 4 and 5 show that the repetitive DNA was over labelled with trans-DDP as a result of which the blocking of hybridisation was made more difficult (ratio 1:2) A non-saturated labelling of trans-DDP is depicted in slides 8 and 9. The best results were obtained with a ratio of 1:1.

Example 2

Blocking Amplification of Specific Sequences During PCR, by Trans-DDP Labelled Dideoxy Primer Two PCR reactions are run in parallel: In the first reaction PCR is performed on plasmid DNA with two sequence-specific primers (primer A and primer B). This reaction yields an amplification product of a defined length. In the second reaction an identical PCR is performed. To the reaction mixture however, also two trans-DDP labelled oligonucleotides are added, which have a dideoxy nucleotide at their 3' end, and which are complementary to sequences within the region that can be amplified by primer A and B. This second reaction will not yield a product, since amplification is blocked by the trans-DDP labelled oligonucleotides.

Example 3

Blocking Repetitive Sequences During DOP-PCR

A DOP-PCR is performed in which amplification of repetitive sequences is blocked by adding trans-DDP labelled nucleotide sequences which lack the 3' hydroxy group and are complementary to several repetitive sequences. With the amplification product an in situ hybridisation experiment on metaphase chromosomes is performed. In comparison to a non-blocked amplification product, this probe gives considerably less background on the non-target chromosomes.

Example 4 a. Two fluorochromes for ratio labelling (n=2), no ratios (r=0) and no binary label (m=0) results in 2 colours, as expected.
b. Three fluorochromes for ratio labelling (n=3), 3 ratios (r=3) and 1 binary label (m=1) results in 24 colours (the situation that will be demonstrated in this paper)
c. Increasing the number of ratios to r=4 and the number of fluorochromes for ratio labelling to 4 results in 28 colours.
d. Each binary fluorochrome results in doubling of the number of colours; that is to 56 (for 1) or to 112 (for 2).

The principle of this concept is demonstrated on 24 human chromosomes using enzymatic labell ing of probes and probe mixi ng to accomplish ratio labelling (fluorescein, lissamine and Cy5 as primary fluorophores and DEAC as combinatorial label), as well as direct attachment of the colour code to the probes using chemical labelling. In the latter DEAC, Cy3 and Cy5 served as primary fluorophores, and Fluorescein or a derivative was used as binary label.

Prodedures

Multi-colour FISH Staining of Human Chromosomes

Preparation of human metaphase chromosomes was performed as described by Wiegant et al. Chromosomes from normal human individuals as well as f rom in vitro cultured JVM-2 cells were used. Probes for all chromosomes were obtained from Cytocell, UK. All probe DNA was amplified by DOP-PCR to generate a set of painting probes for all 24 human chromosomes.

Enzymatic Labelling of Probes

All probes were fluorescently labelled by incorporation of labelled dUTPs either by PCR or nick translation using fluorescein-, digoxigenin-dUTP (Boehringer Mannheim, Germany), lissamine-dUTP (NEN life Science Products, USA) or Cy5-dUTP (Amersham, UK). The digoxygenin-labelled probe s were detected indirectly using diethylaminocoumarin (DEAC, Molecular Probes, USA).

Chemical Labelling of Probes Using ULS (Universal Linkage System): DEAC-ULS, Cy3-ULS and Cy5-ULS were chosen as primary fluorophores and Fluorescein as combinatorial fourth label to demonstrate digoxigenin-ULS (dig-ULS) labelled probes. The following strategy was used to label and dissolve the ULS-labelled probe set:

First, chromosome-specific painting probes for chromosomes 2, 4, 6, 8, 10, 12, 14, 16, 18, 20, 22 and X (100–400 ng) were labelled in one reaction with dig-ULS according to the manufacturers instructions. Thereafter, this probe set was purified on a Qiagen quick spin column (Qiagen Inc., Valencia, Calif., USA ) according to the manufacturers instructions. The labelled probe mixture was eluted from the Qiagen column using 100 µl of 10 mM Tris.HCl pH 8.5.

Second, all chromosome-specific painting probes were fluorescently labelled according to table 2 by mixing 30 µl of the listed ULS compounds (or mixtures thereof) with 1 mg of chromosome-specific painting probe DNA (all from Cytocell) using DEAC-ULS (26.7 µM), Cy3-ULS (20 µM) and Cy5-ULS (13.3 µM) in a final volume of 100 µl of water. In case probes were labelled with mixtures of two different ULS-compounds, the ULS-compounds were first mixed in the desired ratio before the probe DNA was added. After 15 min incubation at 65° C., the labelled probes were purified on Qiagen quick spin columns (Qiagen Inc., Valencia, Calif., USA ). The labelled probes were eluted from the Qiagen columns using 100 µl of 10 µM Tris.HCl pH 8.5. Prior to the hybridisation, fluorescent ULS-labelled probes where combined in amounts as indicated in the right column of Table 2 together with the 100 µl of dig-ULS labelled probe mixture from the first step. This probe mixture was then ethanol precipitated in the presence of 10× excess low molecular weight fish sperm DNA (Boehringer Mannheim), and 3× excess human $C_o t1$-DNA (Gibco, BRL) (an alternative method for suppression of repetitive sequences is presented below). Thereafter the probe mixture was dissolved in 10 µl 50% deionized formamide, 2×SSC, 50 mM sodium phosphate pH 7, 10% dextran sulfate. This 10 µl of probe mixture was used as hybridisation solution.

FISH Staining of Human Metaphase Chromosomes:

Slides with metaphase chromosomes were pre-treated with RNaseA and pepsin according to Wiegant et al. The chromosome preparations were denatured by incubating them 90 sec at 80° C. in 60% formamide, 2×SSC, pH 7 on a hot plate. After removal of the coverslip the slides were dehydrated through an ethanol series and air dried. Then, 10 µl hybridisation mixture was applied under a 18×18 mm coverslip, sealed with rubber cement and hybridisation was performed for 120 hrs at 37° C. in a humid chamber. The hybridisation mixture contained 50% formamide, 2×SSC, 50 mM sodium phosphate pH 7, 10% dextran sulphate, 100–500 ng of each DEAC-, Cy3- and Cy5-labeled probe (both single-and ratio-labelled probes) (see Table 2), 100–400 ng of each dig-ULS labelled probe, 3× excess human $C_o t1$-DNA and 10× excess low molecular weight fish sperm DNA in 10 µl. Before application, the probes were denatured for 10 min at 80° C., followed by 60 min incubation at 37° C. to allow pre-annealing with the 3 times excess of $C_o t1$-DNA. embedded in Vectashield (when enzymatically labelled probes were used) or Citifluor (Agar, Stansted, UK) (when chemically labelled probes were used) prior to microscopical evaluation.

Digital Imaging Microscopy

Digital fluorescence imaging was performed using a Leica DM-RXA epiflourescence microscope (Leica, Wetzlar, Germany) equipped with a 100-W mercury arc lamp and computer controlled filter wheels with excitation and emission filters for visualisation of DEAC, Flourescein, Cy3 and Cy5, using HQ-FITC, Pinkel set plus SP 570, HQ-Cy3, HQ-Cy5 and DEAC filter (Chroma Technology) respectively. DAPI was excited with UV light using block A. A 63x objective (N.A. 32, PL APO, Leica) was used.

Image acquisition was performed as described before. Chromosomes were segmented interactively by thresholding the DAPI image. The segmented image was used as a mask for the colour image, which was composed of the 3 images corresponding with the ratio labelled fluorochromes (green for DEAC, red for Cy3 and blue for Cy5) and of the Fluorescein image. Note that this procedure does not require thresholding of the three colours. The fourth Fluorescein image was evaluated binary, that is chromosomes with or without Fluorescein fluorescence were distinguished. This was performed by finding the optimal threshold in the histogram of the Fluorescein image for the pixels lying within the DAPI mask. Typically, two gaussion distributions were observed, corresponding to Fluorescein positive and negative chromosomes.

Classification was performed in two steps: the chromosome classification was followed by a pixel classification to detect eventual translocations. Chromosome classification was based mainly on the modal colour value of each chromosome, e.g. its position in one of the colour triangles (the one with or without the binary label), as shown in FIG. 1. The shortest distance of the measured modal colour value of a chromosome to the theoretical expected ratio colour of all chromosome classes was therefore calculated. In order to compensate for non-specific fluorescence contributions and to increase the robustness of the method the theoretical expected colour values were warped onto a triangle formed by the measured modal values of the chromosomes with only one ratio colour. Besides the modal colour value also the length of the chromosomes was used for classification. Theoretically, the colour values of the chromosomes should correspond with the original probe ratios. In practice however, a more robust approach is obtained, when a number of metaphases was used for training of the classifier. Following object classification, each pixel within a chromosome was classified on the basis of the shortest distance to the measured chromosome classes. The binary (fourth colour) information of each pixel was used to decide, within which colour triangle distance calculations should be performed. Assignment of classification colours is considered useful and foreseen, but was not implemented in the current software.

Finally, a karyogram was generated based on chromosome classification showing the ratio colours, as described above. A karyogram, in which a pseudo colour was assigned to the corresponding chromosome class of each separate chromosome pixel was produced to facilitate the interactive detection of chromosome translocations. When needed the DAPI banding image was used for comparison purposes.

Results

A 24 colour COBRA staining procedure using four fluorophores was applied to normal and abnormal chromosomes. The optimal conditions for labelling of the probes and the final composition of the probe set required some fine tuning, due to the fact that some probes performed better than others. Typically, less performing FISH probes were given such colour combinations that colour overlap with other probes was minimised.

Optimal staining results were obtained at prolonged hybridisation times (5 days), although three days in many cases was sufficient. The suppression of repetitive sequences was found essential for selective staining of chromosomes. FIG. 2 shows how the 24 chromosomes occupy the colour space. Typically, within a certain chromosome image, signal intensities showed relatively large variations, due to local differences in FISH intensity. The characteristic colour however was sufficiently constant to form clusters, with a defined angle within the three D colour space (FIG. 2). Although some chromosome clusters showed overlap, they were well enough separated to be classified automatically using the procedure described above.

FIG. 3 shows the actual chromosome images and the resulting karygram. Integration times varied depending on the fluorophore used and ranged from 0.5 to 20 sec. An entire Cobra acquisition and analysis procedure typically took approximately 1 min.

Applied to abnormal chromosomes as shown in the JVM cell line, Cobra allowed for easy detection of abnormal chromosomes (FIG. 4). Essential in the ULS mehtod is that in principle each probe molecule contains the ratio code, making mixing obsolete. Ratio labelling of DEAC, Cy3 and Cy5 performed excellent, and could be well combined with binary fluorescein labelling. Results obtained with these probes are shown in FIG. 5.

The robustness of COBRA depended on the quality of the metaphase chromosomes obtained, as is the case for both automated analysis of Giemsa banded and FISH stained chromosomes. Good quality slides always resulted in images of good signal to noise ratio that could be classified automatically, whereas user intervention increased with decreasing staining quality.

The Cobra principle combines the advantages of ratio labelling and binary labelling. It "settles" for making ratios of two fluorophores only, but utilises the possibility of doubling the number of colours by introducing indirectly labelled haptens, that require a binary decision only. As shown, this approach is feasible and allows for identifying 24 human chromosomes using 4 fluorophores only.

The full potential of this approach has not been explored yet. So far only painting probes were used in Cobra. Considering the short exposure times, we anticipate that other type of probes such as YACs or PACs can be used in a similar approach.

As the mathematical equation shows, the number of colours particularly increases if more dyes or more ratios are used for the primary colour set. It has been shown that distinction of 6 or 7 ratio of two dyes is feasible.

Such an approach is best achievable if chemical labelling is used. The ULS is advantageous for large scale production of quality controlled painting probes. In this context the COBRA strategy for efficient use of fluorophores can significantly contribute to a further increase of MFISH multiplicity and thereby to further exploitation in cytogenetics.

Example 5

Prevention of Cross-hybridisation Between Different HPV Types

Background: The KREATECH HPV typing probe 31, 33 gives on CaSki cells a weak though clear hybridisation signal. CaSki cells are HPV16. Can through the use of trans-DDP this undesired hybridisation be prevented?
Scheme: select homologues sequences between HPV16 on the one hand and HPV31 and 33 on the other hand. Label these sequences with trans-DDP and irreversible cross-link these sequences after hybridisation. The remaining sequences are HPV31 and/or 33 specific. After hybridisation with this DIG-ULS labelled remaining fraction on CaSki cells no hybridisation is expected.

Example 6

Use of Trans-DDP in Filter Hybridisations

Background: The prevention of hybridisation between sequences that make the interpretation of the end result difficult. For example repetitive sequences (for example in an intron) that mask the signal of single copy. Or the suppression of generally present sequences in a stage specific cDNA library favouring of stage specific unique sequences (can be compared with subtractive hybridisations).

Scheme: HPV16 is cloned in pSP64. After digestion with a restriction enzyme that removes the insert from the plasmid, both fragments are separated on agarose gel en blotted on a filtermembrane. As probe the plasmid and the insert are labelled with DIG-ULS. When this is used as such, two bands are acquired after a hybridisation, i.e. the HPV16 en the pSP64 bands. However, through the addition of trans-DDP labelled pSP64 DNA will the pSP64 sequences be irreversibly cross-linked and even after denaturation they will not be capable anymore of taking part in the subsequent hybridisation. As a result of this hybridisation only one predominant band is expected, i.e. the one specific for HPV16 (this in the ideal case). This example describes a cross-linking of homologues sequences in solution. Reversal of the system and first performing a matrix hybridisation with trans-DDP pSP64 and subsequently after stripping of the filter a DIG-ULS pSP64/HPV16 hybridisation will result in a comparable result.

Example 7

In this example one aspect of the Cobra principle is implemented with TRANS-ULS labelled probes in an application using mFISH.

For the generation of a human chromosome 4 or chromosome 20 specific probe, a DOP-PCR is performed on human chromosome 4 or chromosome 20 preparations according to the procedure described in Multi-colour FISH staining of human chromosomes, in which amplification of repetitive sequences is blocked by adding trans-DDP labelled nucleotide sequences which lack the 3' hydroxy group and are complementary to several repetitive sequences. The chromosome 4 specific probe was ratio labelled with DEAC-ULS and Cy3-ULS (50:50) according to the procedure described in Chemical labelling of probes using ULS. The chromosome 20 specific probe was ratio labelled with DEAC-ULS and Cy3-ULS (50:50) and combinatorial labelled with Fluorescein according to the procedure described in Chemical labelling of probes using ULS.

Slides with metaphase chromosomes spreads of JVM-2 cells were prepared and FISH- stained according to the procedure described in FISH staining of human metaphase chromosomes.

Results were visualised according to the procedure described under imaging microscopy.

When using the trans-ULS probes optimal staining results were obtained after surprisingly short hybridisation times, compared to the non-trans-ULS probes, in for instance example 4.

Overnight hybridisation was often sufficient for staining. Whereas for optimal results using non trans-ULS FISH-techniques as in example 4 hybridisation times of five days are optimal. The cobra labelling allowed clear and unambiguous typing of chromosome 4 and chromosome 20 in metaphase spreads of JVM-2 cells following overnight hybridisation with the probes.

Example 8

Blocking Hybridisation of Fluorophore Labelled Repetitive DNA by Trans-DDP Labelled Repetitive DNA In this example we in essence repeated the experiments described in example 1. A flourescein-ULS labelled human chromosome 1 specific probe was hybridised in situ onto human metaphase chromosome spreads. For a person skilled in the art it is obvious that this type of probe contains non chromosome specific repetitive DNA sequences. Hybridisation of these sequences was hindered often by adding excess of unlabelled human Cotl DNA. Here use is made of trans-DDP labelled repetitive DNA sequences to suppress hybridisation of non chromosome specific repetitive sequences present in a chromosome specific probe. All slides but one were denatured and pre-incubated w ith trans-DDP labelled human repetitive DNA. The ratio repetitive DNA:trans-DDP is given in table 1. Subsequently, all slides but one were denatured and fluorescein-ULS labelled probe was added to all slides. Hybridisation of trans-DDP labelled repetitive DNA to its target created a stable interstrand connection, preventing hybridisation of flourescein-ULS labelled DNA. Therefore, the intensity of the flourescein singal on the chromosomes is reduced (see table 1 for details). Slides 1, 2 and 3 are control slides. For the slides 2 and 3, no trans-DDP was used and there was no cross-linking. Thus, the acquired results have to be seen as references values. The results of slides 4 and 5 show that the repetitive DNA was over labelled with trans-DDP as a result of which the blocking of hybridisation was made more difficult (ratio 1:2). A non-saturated labelling of trans-DDP is depicted in slides 8 and 9. The best results were obtained with a ratio of 1:1 (slides 6). For experimental details about ULS probe labelling in situ hybridisation see example 4.

Example 9

Blocking Amplification of Specific Sequences During PCR by Trans-DDP Labelled Primers In this example we in essence repeated the experiments described in example 2. Human Papillomavirus (HPV) type 16 primers HPVfor (5'-TCAAAAGCCACTGTGTCCTG-3') and HPVrev (5'-AACCACCCCCACTTCCAC-3') yielded a fragment of 945 bp in a polymerase chain reaction (PCR). Four internal primers were designed: primer TU16for1 (5'-AGAGCTGCAAAAAGGAGATTATTTGAAAGCGA-3'), primer TU16for2 (5'-AGAGACAACTGATCTCTACTGTTATGAGCA-3'), primer TU16rev1 (5'-TCCTGTGCAGTAAACAACGCATGTGCTGTC-3'), and primer TU16rev2 (5'-CGTGTGTGCTTTGTACGCCACAACCGAAGCGTAGAGT-3'). These internal primers were pooled (0.125 µg/µl each). The primer mixture was labelled with 50 ng trans-ULS per µg primers according to the standard ULS labelling protocol. Next, the oligonucleotide mix was column purified in order to remove free trans-ULS. Total genomic HPV 16 DNA (40 ng final) was mixed with trans-ULS labelled internal primers (120–160 ng final) in a solution of 6×SSC. This solution was denatured and incubated at 60° C. for 1 hour. This step was repeated two more times and was followed by a column purification. Subsequent, a PCR amplification was carried out as follows: a PCR master mix consisting of a PCR buffer, HPVfor and HPVrev primers (10 µM each, dNTPs (2.5 mM each), and Taq DNA polymerase (5 units) was added to a 0.5 ml PCR tube containing either (i) HPV 16 genomic DNA only, (ii) HPV 16 DNA and internal primers, or (iii) HPV 16 DNA cross-linked with trans-ULS labeled internal primers. The PCR profile was: 95° C. for 2 minutes, 23 cycles of 95° C. for 45 seconds; 57° C. for 45 seconds; 72° C. for 1 minute, and 1 cycle of 95° C. for 45 seconds; 57° C. for 45 seconds; 72° C. for 15 minutes. Ten µl of each PCR amplified mix was run on a 1% agarose gel (see FIG. 6). Lane 1 shows the 945 bp fragment (see above). The yield of the 945 bp fragment was reduced when the internal primers were added to the PCR mix (lane 2). When use was made of trans-ULS labeled internal primers no 945 bp PCR fragment was amplified. Irreversible cross-linking of the internal primers blocked the DNA polymerase chain elongation at well defined positions within the 945 bp fragment. Similar results can be obtained when use is made of trans-ULS labelled dideoxy internal primers.

Example 10

Blocking Repetitive Sequences During DOP-PCR and Use of Such Probes in In Situ Hybridisation.

In this example we in essence repeated the experiments described in example 3. Human $C_o t$ 1 DNA was end labelled with ddATP according to the following protocol: 50 pg of $C_o t$ 1 DNA was denatured at 90° C. for 10 minutes and mixed with TdT buffer, ddATP, and TdT (terminal transferase). The mixture was incubated at 37° C. over night and ethanol precipitated. Next, the 3'-ddATP human $C_o t$ 1 DNA was labelled with the cross-linking agent trans-ULS. Five µg of the DNA was mixed with various amounts of trans-ULS, incubated at 85° C. for 30 minutes, and column purified. Best results were obtained with the 3'-ddATP human $C_o t$ 1 DNA:trans-ULS ratio of 1:0.3. The FISH result of this sample is presented below. Human chromosome 1 painting probe was mixed with trans-ULS labelled 3'-ddATP human $C_o t$ 1 DNA (10 fold excess), denatured and allowed to hybridise and interstrand cross-link at 65° C. overnight. Next, a small aliquot of this sample was PCR amplified in two consecutive PCR rounds, purified, and labelled with Cy3-ULS all according to standard procedures. The chromosome 1 probe produced in this way is deprived of high copy repetitive sequences (in this particular example human $C_o t$ 1 DNA homologous sequences) . This type of probe eliminates the use of human $C_o t$ 1 DNA to suppress cross-hybridisation of these repeats in in situ hybridisation experiments. The applicability of the Cy3-ULS labelled repeat free human chromosome 1 probe was demonstrated in FISH. The in situ hybridisation was essentially the same as described in example 4 and/or 12. The results are shown in FIG. 7. A high degree of non chromosome specific cross-hybridisation was seen when use was made of the chromosome 1 probe not deprived of high copy repetitive sequences without addition of human $C_o t$ 1 DNA (FIG. 7A). Addition of five fold excess of human $C_o t$ 1 DNA largely suppressed non chromosome specific cross-hybridisation. Human chromosome 1 could clearly be identified (FIG. 7B). Suppression of non chromosome specific cross-hybridisation, without the need of large amounts of suppressor DNA (in this case human $C_o t$ 1 DNA), was obtained with probes as described in this invention. Chromosome 1 could be clearly identified when use was made of the trans-ULS treated repeat deprived chromosome 1 specific probe (FIG. 7C).

Example 11

Prevention of Cross-hybridisation Between Different Human Papillomavirus Types

In this example we in essence repeated the experiments described in example 5. Several Human Papillomavirus (HPV) types show a high degree of identity between their nucleotide sequences. For example, HPV 18 and HPV 45 genomes show an identity of 79.7%. The generation of a HPV 45 specific probe free of HPV 18 homologous sequences can be made possible through the use of a cross-linking agent. HPV 45 total genomic DNA was labelled with DIG-ULS according to the standard ULS labelling procedure. HPV 18 total genomic DNA was sonicated, biotin end labelled, and labelled with trans-DDP at a DNA:trans-ULS ratio of 1:1. The labelled DNAs were column purified and mixed according to the following scheme:

Tube 1: DIG-ULS labelled HPV 45+unlabelled HPV 18 (sonicated)

Tube 2: DIG-ULS labelled HPV 45+biotinylated and trans-DDP labelled HPV 18

The ratio HPV 45: HPV 18 was 1:10 in both tubes. The DNAs, dissolved in a solution of 6×SSC (final concentration), were denatured and incubated at 65° C. for 5 hours. Streptavin coated magnetic beads were added to these tubes and biotinylated DNAs were removed from the solution. Consequently, tube 2 contains mainly DIG-ULS labelled HPV45 DNA deprived from HPV 18 homologous sequences. The probes were denatured and mixed with DIGEASYHYB solution at a final concentration of 25 ng/ml. HPV 45 and HPV 18 genomic DNA was spot blotted onto nylon membrane strips at concentrations ranging from 1000 pg to 0.1 pg. Probe mixes were added to the target strips and allowed to hybridise over night at 42° C. The result is shown in FIG. 8. The DIG-ULS labelled HPV 45 probe hybridises to itself irrespective of the presence of unlabelled homologous HPV 18 DNA (lane 1). DIG-ULS labelled HPV 45 unique sequences do hybridise to HPV 45 total genomic DNA but the signal is less strong due to a reduced probe size (lane 2). DIG-ULS HPV 45 labelled unique sequences do not hybridise to HPV 18 total genomic DNA under the condition used in this experiment (lane 3).

Example 12

Use of Trans-DDP in Filter Hybridisation

In this example we in essence repeated the experiments described in example 6. A cocktail of five oligonucleotides was labelled with 0.05 µg trans-ULS per µg DNA according to the standard ULS labelling procedure. Next, the trans-ULS labelled oligo cocktail was allowed to pre-hybridise with a cocktail of complementary Biotin-ULS labelled oligonucleotides (25 ng) at 65° C. over night. The trans-ULS labelled oligo cocktail was added at a five fold or ten fold excess, respectively. After being denatured these mixes were added to DIGEASYHYB buffer at a final concentration of 25 ng/ml of Biotin labelled complementary oligonucleotides. These mixes were allowed to hybridise at 37° C. for 6 hours to the cocktail of five oligonucleotides which were spotted onto nylon strips at various quantities ranging from 10000 to 1 pg. Hybridisation was visualised through the use of alkaline phosphatase labelled streptavidin and subsequent chemiluminescence detection. The results are shown in FIG. 9. The following samples served as controls: (i) Biotin labelled complementary oligonucleotide cocktail not incubated with the trans-ULS labelled oligonucleotide cocktail (lane 1), and (ii) Biotin labelled complementary oligonucleotide cocktail pre-incubated with a 5 fold and 10 fold excess of the oligonucleotide cocktail (no trans-ULS) (lane 2 and 4, respectively). Lane 3 and 5 clearly show the effect of the cross-linking compound. The hybridisation signals are very weak and significantly less compared to the controls.

Example 13

Combined Binary Ratio Labelling

In this example we in essence repeated the experiments described in example 4.

a. Two fluorochromes for ratio labelling (n=2), no ratios (r=0) and no binary label (m=0) results in 2 colours, as expected.

b. Three fluorochromes for ratio labelling (n=3), 3 ratios (r=3) and 1 binary label (m=1) results in 24 colours (the situation that will be demonstrated in this example)

c. Increasing the number of ratios to r=4 and the number of fluorochromes for ratio labelling to 4 results in 28 colours.

d. Each binary fluorochrome results in doubling of the number of colours; that is to 56 (for 1) or to 112 (for 2).

The principle of this concept is demonstrated on 24 human chromosomes using enzymatic labelling of probes and probe mixing to accomplish ratio labelling (fluorescein, lissamine and Cy5 as primary fluorophores and DEAC as combinatorial label), as well as direct attachment of the colour code to the probes using chemical labelling. In the latter DEAC, Cy3 and Cy5 served as primary fluorophores, and Fluorescein or a derivative was used as binary label.

Procedures

I. Multi-colour FISH Staining of Human Chromosomes

Preparation of human metaphase chromosomes was performed as described by Wiegant et al (1993). Chromosomes from normal human individuals as well as from in vitro cultured JVM-2 cells were used. Probes for all chromosomes were obtained from Cytocell, UK. All probe DNA was amplified by DOP-PCR to generate a set of painting probes for all 24 human chromosomes.

II. Enzymatic Labelling of Probes

All probes were fluorescently labelled by incorporation of labelled dUTPs either by PCR or nick translation using fluorescein-, digoxigenin-dUTP (Boehringer Mannheim, Germany), lissamine-dUTP (NEN Life Science Products, USA) or Cy5-dUTP (Amersham, UK). The digoxygenin-labelled probes were detected indirectly using diethylaminocoumarin (DEAC, Molecular Probes, USA).

III. Chemical Labelling of Probes Using ULS (Universal Linkage System)

DEAC-ULS, Cy3-ULS and Cy5-ULS were chosen as primary fluorophores and Fluorescein as combinatorial fourth label to demonstrate digoxigenin-ULS (DIG-ULS) labelled probes. The following strategy was used to label and dissolve the ULS-labelled probe set:

First, chromosome-specific painting probes for chromosomes 2, 4, 6, 8, 10, 12, 14, 16, 18, 20, 22 and X (100–400 ng) were labelled in one reaction with DIG-ULS according to the manufacturers instructions. Thereafter, this probe set was purified on a Qiagen quick spin column (Qiagen Inc., Valencia, Calif., USA) according to the manufacturers instructions. The labelled probe mixture was eluted from the Qiagen column using 100 µl of 10 mM Tris.HCl pH 8.5.

Second, all chromosome-specific painting probes were fluorescently labelled according to table 2 by mixing 30 µl of the listed ULS compounds (or mixtures thereof) with 1 mg of chromosome-specific painting probe DNA using DEAC-ULS (26.7 µM), Cy3-ULS (20 µM) and Cy5-ULS (13.3 µM) in a final volume of 100 µl of water. In case probes were labelled with mixtures of two different ULS-compounds, the ULS-compounds were first mixed in the desired ratio before the probe DNA was added. After 15 min incubation at 65° C., the labelled probes were purified on Qiagen quick spin columns (Qiagen Inc., Valencia, Calif., USA). The labelled probes were eluted from the Qiagen columns using 100 µl of 10 mM Tris.HCl pH 8.5. Prior to the hybridisation, fluorescent ULS-labelled probes where combined in amounts as indicated in the right column of Table 2 together with the 100 µl of DIG-ULS labelled probe mixture from the first step. This probe mixture was then ethanol precipitated in the presence of 10× excess low molecular weight fish sperm DNA (Boehringer Mannheim), and 3× excess human $C_o t$ 1 DNA (Gibco, BRL). Thereafter the probe mixture was dissolved in 10 μl 50% deionized formamide, 2×SSC, 50 mM sodium phosphate pH 7, 10% dextran sulfate. This 10 μl of probe mixture was used as hybridisation solution.

IV. FISH Staining of Human Metaphase Chromosomes

Slides with metaphase chromosomes were pre-treated with RNaseA and pepsin according to Wiegant et al (1991). The chromosome preparations were denatured by incubating them 90 sec at 80° C. in 60% formamide, 2×SSC, pH 7 on a hot plate. After removal of the coverslip the slides were dehydrated through an ethanol series and air dried. Then, 10 μl hybridisation mixture was applied under a 18×18 mm coverslip, sealed with rubber cement and hybridisation was performed for 120 hrs at 37° C. in a humid chamber. The hybridisation mixture contained 50% formamide, 2×SSC, 50 mM sodium phosphate pH 7, 10% dextran sulphate, 100–500 ng of each DEAC-, Cy3- and Cy5-labeled probe (both single- and ratio-labelled probes) (see Table 2), 100–400 ng of each DIG-ULS labelled probe, 3× excess human $C_ot$ 1 DNA and 10× excess low molecular weight fish sperm DNA in 10 μl. Before application, the probes were denatured for 10 min at 80° C., followed by 60 min incubation at 37° C. to allow pre-annealing with the 3 times excess of $C_ot$ 1 DNA. After a 10 min post-hybridisation wash in 2×SSC/0.1% Tween 20 at 370° C. to remove the coverslips, the slides were washed 2×5 min in 50% formamide, 2XSSC, pH 7 at 44° C. This was followed by 2 washes (5 min each) in 0.1×SSC at 60° C. and a 5 min wash at RT in TNT (0.1 M Tris.HCl pH 7.4, 0.15 M NaCl, 0.05% Tween 20). The DIG-ULS labelled probes were detected with a mouse monoclonal antibody against digoxin (Sigma) followed by a rabbit anti mouse antibody conjugated to FITC (Sigma). Chromosomes were counterstained with DAPI. The slides were embedded in Vectashield® (when enzymatically labelled probes were used) or Citifluor® (Agar, Stansted, UK) (when chemically labelled probes were used) prior to microscopical evaluation.

V. Digital Imaging Microscopy

Digital fluorescence imaging was performed using a Leica DM-RXA epifluorescence microscope (Leica, Wetzlar, Germany) equipped with a 100-W mercury arc lamp and computer controlled filter wheels with excitation and emission filters for visualisation of DEAC, Fluorescein, Cy3 and Cy5, using HQ-FITC, Pinkel set plus SP 570, HQ-Cy3, HQ-Cy5 and DEAC filter (Chroma Technology) respectively. DAPI was excited with UV light using block A. A 63x objective ((N.A. 1.32, PL APO, Leica) was used. Image acquisition and analysis was performed on a Cytovision workstation (Applied Imaging, Sunderland, UK). This system consists of a PC (Pentium 133 MHz processor, 24 Mb Ram, 2.1 Gb disc and 17" display) interfaced to a Coolview camera (Photonic Science). The camera has thermo-electric cooling, which allows on chip integration up to circa 30 seconds. Images are digitised in an 8-bit 768×512 image format.

Chromosomes were segmented interactively by thresholding the DAPI image. The segmented image was used as a mask for the colour image, which was composed of the 3 images corresponding with the ratio labelled fluorochromes (green for DEAC, red for Cy3 and blue for Cy5) and of the Fluorescein image. Note that this procedure does not require thresholding of the three colours. The fourth Fluorescein image was evaluated binary, that is chromosomes with or without Fluorescein fluorescence were distinguished. This was performed by finding the optimal threshold in the histogram of the Fluorescein image for the pixels lying within the DAPI mask. Typically, two gaussion distributions were observed, corresponding to Fluorescein positive and negative chromosomes. Classification was performed in two steps: the chromosome classification was followed by a pixel classification to detect eventual translocations. Chromosome classification was based mainly on the modal colour value of each chromosome, e.g. its position in one of the colour triangles (the one with or without the binary label), as shown in FIG. 1. The shortest distance of the measured modal colour value of a chromosome to the theoretical expected ratio colour of all chromosome classes was therefore calculated. In order to compensate for non-specific fluorescence contributions and to increase the robustness of the method the theoretical expected colour values were warped onto a triangle formed by the measured modal values of the chromosomes with only one ratio colour. Besides the modal colour value also the length of the chromosomes was used for classification. Theoretically, the colour values of the chromosomes should correspond with the original probe ratios. In practice however, a more robust approach is obtained, when a number of metaphases was used for training of the classifier. Following object classification, each pixel within a chromosome was classified on the basis of the shortest distance to the measured chromosome classes. The binary (fourth colour) information of each pixel was used to decide, within which colour triangle distance calculations should be performed. Assignment of classification colours is considered useful and foreseen, but was not implemented in the current software. Finally, a karyogram was generated based on chromosome classification showing the ratio colours, as described above. A karyogram, in which a pseudo colour was assigned to the corresponding chromosome class of each separate chromosome pixel was produced to facilitate the interactive detection of chromosome translocations. When needed the DAPI banding image was used for comparison purposes.

Results

A 24 colour COBRA staining procedure using four fluorophores was applied to normal and abnormal chromosomes. The optimal conditions for labelling of the probes and the final composition of the probe set required some fine tuning, due to the fact that some probes performed better than others.

Typically, less performing FISH probes were given such colour combinations that colour overlap with other probes was minimised.

Optimal staining results were obtained at prolonged hybridisation times (5 days), although three days in many cases was sufficient. The suppression of repetitive sequences was found essential for selective staining of chromosomes.

FIG. 2 shows how the 24 chromosomes occupy the colour space. Typically, within a certain chromosome image, signal intensities showed relatively large variations, due to local differences in FISH intensity. The characteristic colour however was sufficiently constant to form clusters, with a defined angle within the three D colour space (FIG. 2). Although some chromosome clusters showed overlap, they were well enough separated to be classified automatically using the procedure described above.

FIG. 3 shows the actual chromosome images and the resulting karyogram. Integration times varied depending on the fluorophore used and ranged from 0.5 to 20 sec. An entire COBRA acquisition and analysis procedure typically took approximately 1 min.

Applied to abnormal chromosomes as shown in the JVM cell line, COBRA allowed for easy detection of abnormal chromosomes (FIG. 4). Essential in the ULS method is that in principle each probe molecule contains the ratio code, making mixing obsolete. Ratio labelling of DEAC, Cy3 and Cy5 performed excellent, and could be well combined with binary fluorescein labelling. Results obtained with these probes are shown in FIG. 5.

The robustness of COBRA depended on the quality of the metaphase chromosomes obtained, as is the case for both automated analysis of Giemsa banded and FISH stained chromosomes. Good quality slides always resulted in images of good signal to noise ratio that could be classified automatically, whereas user intervention increased with decreasing staining quality.

The COBRA principle combines the advantages of ratio labelling and binary labelling. It "settles" for making ratios of two fluorophores only, but utilises the possibility of doubling the number of colours by introducing indirectly labelled haptens, that require a binary decision only. As shown, this approach is feasible and allows for identifying 24 human chromosomes using 4 fluorophores only.

The full potential of this approach has not been explored yet. So far only painting probes were used in COBRA. Considering the short exposure times, we anticipate that other type of probes such as YACs or PACs can be used in a similar approach.

As the mathematical equation shows, the number of colours particularly increases if more dyes or more ratios are used for the primary colour set. It has been shown that distinction of 6 or 7 ratio of two dyes is feasible.

Such an approach is best achievable if chemical labelling is used. The ULS is advantageous for large scale production of quality controlled painting probes. In this context the COBRA strategy for efficient use of fluorophores can significantly contribute to a further increase of MFISH multiplicity and thereby to further exploitation in cytogenetics.

Example 14

COBRA with Repeat Free Whole Chromosome Probes

In this example one aspect of the COBRA principle is implemented with trans-ULS labelled probes in a mFISH application. In this example we in essence repeated the experiments described in example 7.

For the generation of a human chromosome 1 and chromosome 8 specific probe deprived of repetitive sequences a DOP-PCR was performed on human chromosome 1 and chromosome 8 preparations according to the procedure described in example 2.

Amplification of repetitive sequences was blocked by trans-DDP labelled complementary repetitive nucleotide sequences which lacked the 3' hydroxy group. Labelling of probes was as described in chemical labelling of probes using ULS in example 4. The chromosome 8 specific probe was ratio labelled with Cy3-ULS and Cy5-ULS (50:50). The chromosome 1 specific probe was ratio labelled with Cy3-ULS and Cy5-ULS (50:50) and combinatorial labelled with dGREEN-ULS.

Slides with metaphase chromosomes spreads were prepared and FISH-stained according to the procedure described in FISH staining of human metaphase chromosomes in example 4. Results are depicted in FIG. 10.

When using the trans-ULS probes optimal staining results were obtained after surprisingly short hybridisation times, compared to the non-trans-ULS probes, in for instance example 4. Overnight hybridisation was often sufficient for staining whereas for non trans-ULS FISH-techniques, as in example 4, hybridisation times of several days are optimal. The COBRA labelling allowed clear and unambiguous typing of chromosome 1 and chromosome 8 in metaphase spreads following overnight hybridisation with the probes.

Example 15

COBRA Based Labelling of Proteins

In resemblance with COBRA labelling and detection of nucleic acids the COBRA method offers the possibility to detect many proteins simultaneously, even when the number of labels available is limited (less then the number of proteins to be investigated). Important is the broad applicability of the ULS labelling technology in labelling bio-organic molecules.

This example demonstrates both the successful use of ULS labels in labelling proteins and shows proof of principle of COBRA labelling and detection of proteins.

The proteins that are going to be detected in this example are avidin and bovine serum albumin (BSA).

These two proteins were single and multiple labelled with ULS labels in an aqueous solution at physiological conditions.

The labels with which the proteins were labelled are Flu-ULS (fluorescein), DNP-ULS (dinitrophenol), and DIG-ULS (digoxigenin). The labels used for ratio labelling were Flu and DNP. Digoxigenin was the binary label.

The generation of the various labelling solutions was performed as follows.

For single labelling of avidin or BSA, which served as a control for the labelling of proteins with ULS per se, the label consisted of 1 mg/ml of either Flu-ULS, DNP-ULS or DIG-ULS.

For ratio labelling the label consisted of Flu-ULS and DNP-ULS, mixed in a 1:1 ratio.

For the combined ratio-binary labelling, the labelling mixture consisted of the ratio labels+the binary label (DIG-ULS) in an equimolar amount.

The proteins were incubated with the labels according to the description below.

Each protein (2 µg/µl in 0.5 PBS) was labelled by mixing 50 µl of the protein solution with 50 pl of a stock solution of 1 mg/ml label in 0.5×PBS of the single label either Flu-ULS, DNP-ULS or DIG-ULS the ratio-label (Flu-ULS:DNP-ULS)

the ratio-binary label (Flu-ULS:DNP-ULS+DIG-ULS)

Labelling was performed at 37° C. for 1 hour. The ULS labelled proteins were spotted on nitrocellulose membranes. The solutions containing the labelled protein were spotted on several strips (1 µl per spot). Next the spots were air dried and subsequently the filters were blocked for 15 min. in blocking solution (1×Blocking medium of Boehringer Mannheim, cat no. 1 585 762) in the maleic buffer according to the manufactures instructions. Next, the filters were incubated in a solution comprising the same blocking solution, 1 mg/ml BSA, and alkaline phosphatase (AP) labelled antibodies. The antibodies used are alkaline phosphatase labelled antibodies specific for digoxigenin (sheep anti-digoxigenin-AP; 1:5000; Roche Molecular Biochemicals 1 093 274), dinitrophenol (rabbit anti-DNP-AP; 1:1000; Sigma D5103), and fluorescein (sheep anti-fluorescein-AP; 1:5000; Roche Molecular Biochemicals 1 426 338). This incubation took place at room temperature for 30 min. Next, the filters were washed 3 times for 5 min. in TNT buffer followed by 2 washes in water for 2 min. each. The NBT/SCIP detection system for AP was applied according to the manufactures instructions. The AP reaction was allowed to take place for 16 hours in the dark at room temperature. The reaction was stopped by washing the filters in 1×TE buffer for 15 min.

The results are shown in Table 3.

Column Av-Flu combined with rows 1–4 of table 3 depicts the results of avidin labelled with Flu-ULS and detected with AP labelled antibodies. Only those spots showed a clear positive signal where AP anti-Flu was present. This demonstrates that avidin was successfully labelled with Flu-ULS.

Taken together, and in a similar fashion, Table 3 shows that both avidin and BSA could be labelled with the different labels as described above. Also, the proteins could be labelled with various ULS labels simultaneously. In this particular example the two proteins could not be distinguished from each other based on their ratio labels only (Table 3, row 3 and 7). Labelling one protein in a binary fashion made possible to distinguish the two proteins (Table 3, row 4 and 9).

Table 3 shows that both proteins can be labelled with different ULS labels and COBRA labelling could be successfully applied to proteins.

Alternatively, simultaneous detection of proteins labelled according to the COBRA principle can be made possible through the use of label specific detection systems. Note that the principle of COBRA labelling is independent of the type of target molecules.

(a): three primary colours (fluorescein, lissamine, Cy 5); without binary DEAC label;
(b): idem, with binary DEAC label.

Figure 1:
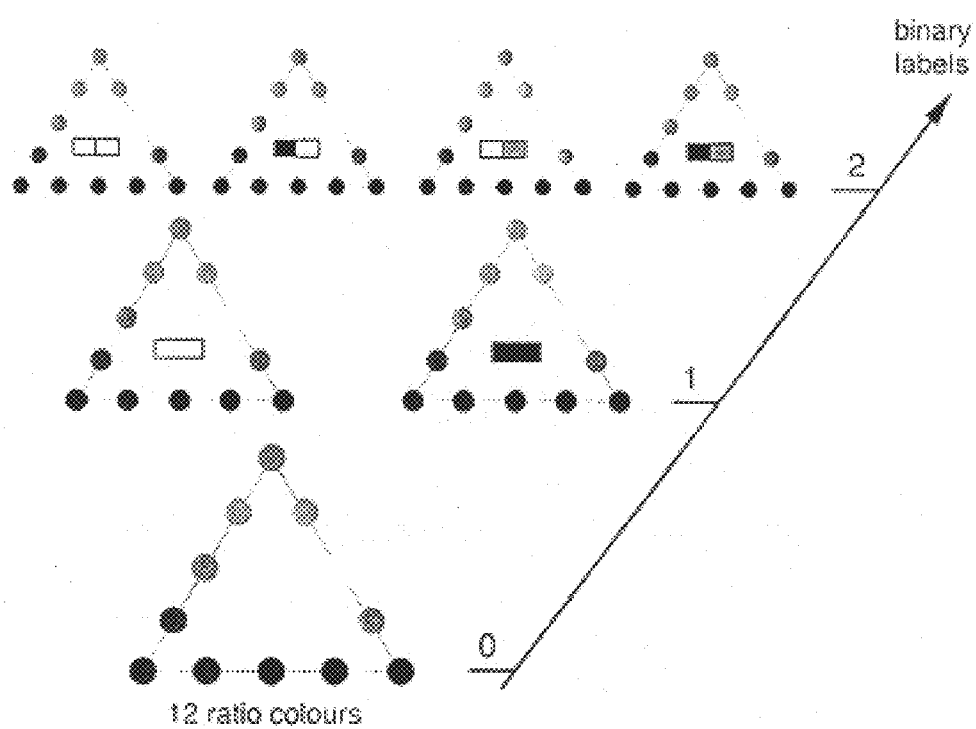
FIG. 1: Principle of COBRA. The primary set of 12 ratio colours is doubled each time an independent binary label is introduced, resulting in 24 colours for 1 hapten, and in 48 colours for 2 haptens.

Note: FIG. 1 is a schematic top view of the 2×12 clusters seen at equal x,y,z values of the measured data shown in this figure.

Figure 2:
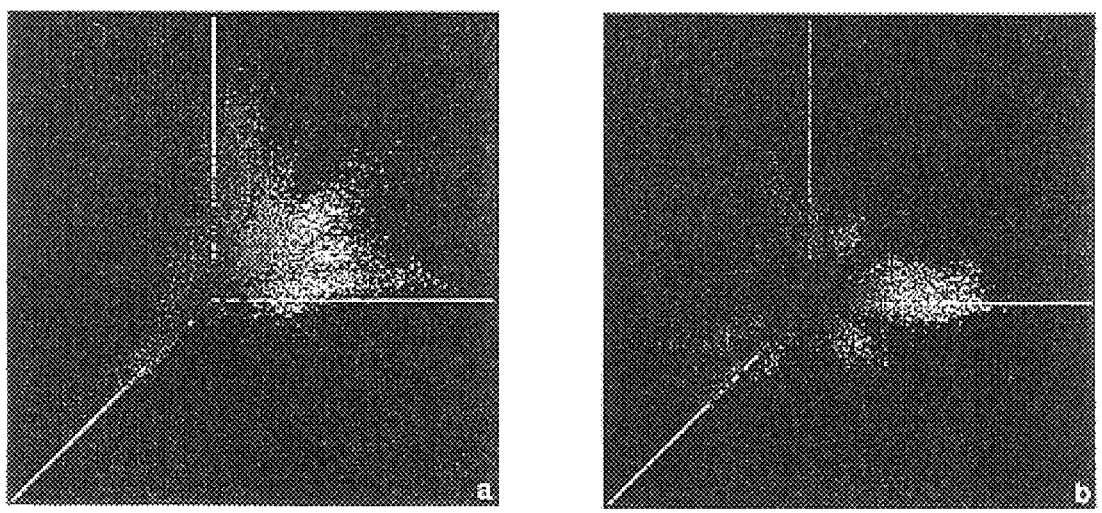
FIG. 2: Human chromosomes were stained in 24 colours using the COBRA principle. For each of the 24 chromosomes the fluorescence intensity was plotted in a three dimensional colour space. Each coloured dot represents the measured colour intensity of an image point (pixel) of a certain chromosome.
Figure 3:
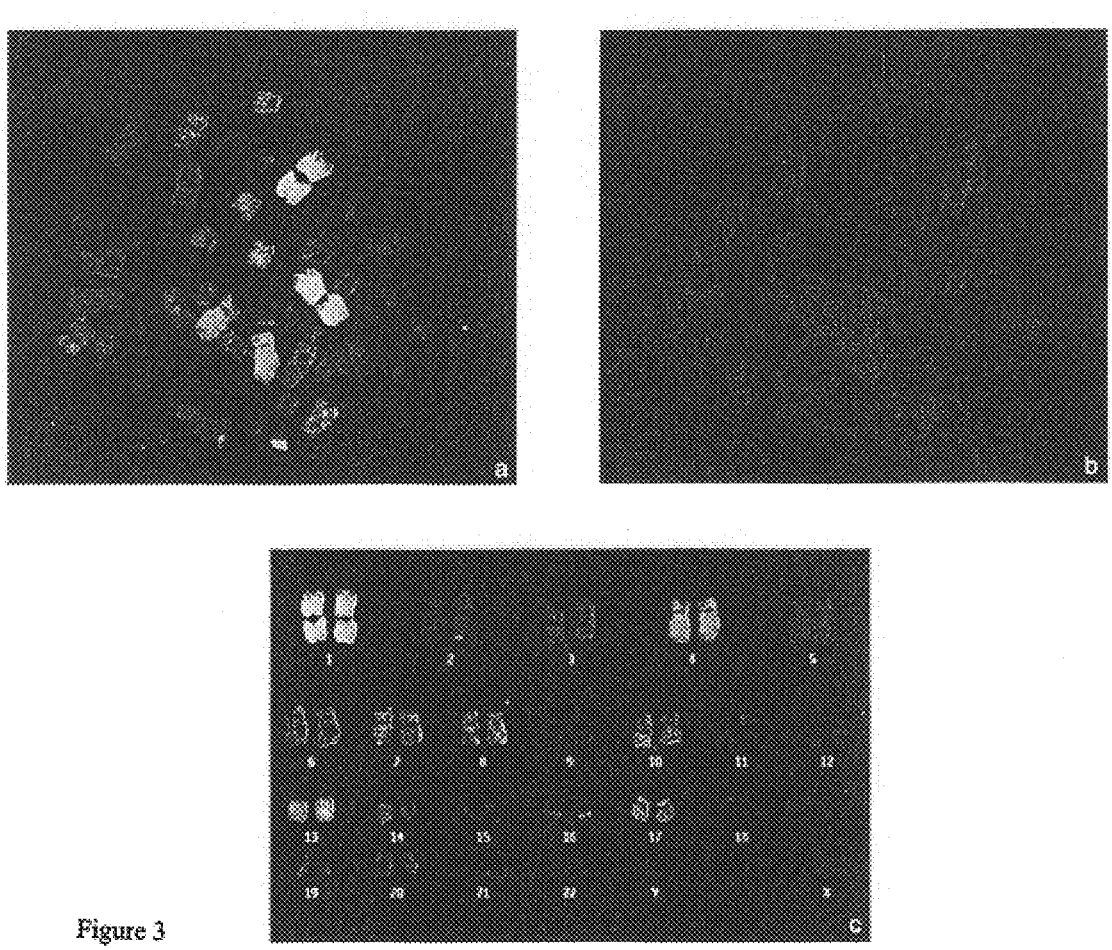

FIG. 3: Normal human chromosomes labelled by COBRA in 24 colours (same data as FIG. 2).
(a) Image (12 colours) resulting from the three primary dyes used in ratio labelling;
(b) DEAC image of the same metaphase cell;
(c) Karyogram resulting from the combination of image (a) and
(b) and automated classification FIG. 4: COBRA (24 colours) applied to a JVM cell line (B-prolymphocytic leukemia) showing translocations t(11, 14), t(3,8) and t(1,15).

Figure 5:
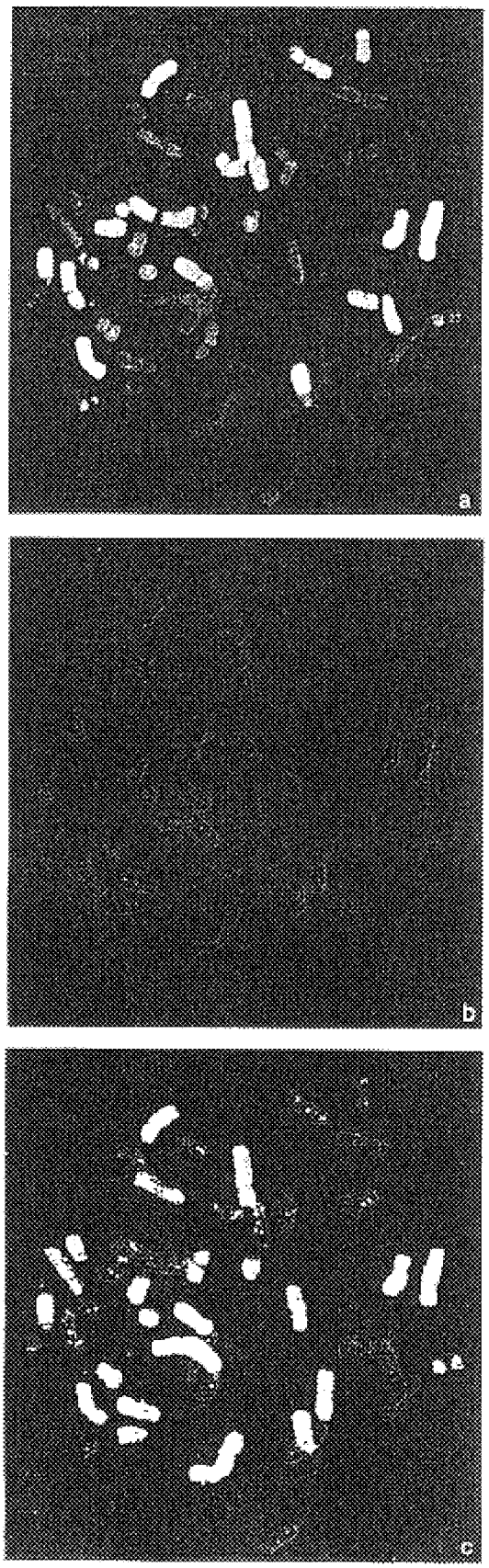

FIG. 5: Results of ratio labelling obtained using chemical labelling (ULS system). The fluorophores DEAC, Cy3 and Cy5 were used as primary labels for ratio labelling. The DIG-ULS labelled second set of 12 probes was demonstrated indirectly using fluorescein labelled immunoconjugates.

Figure 4:
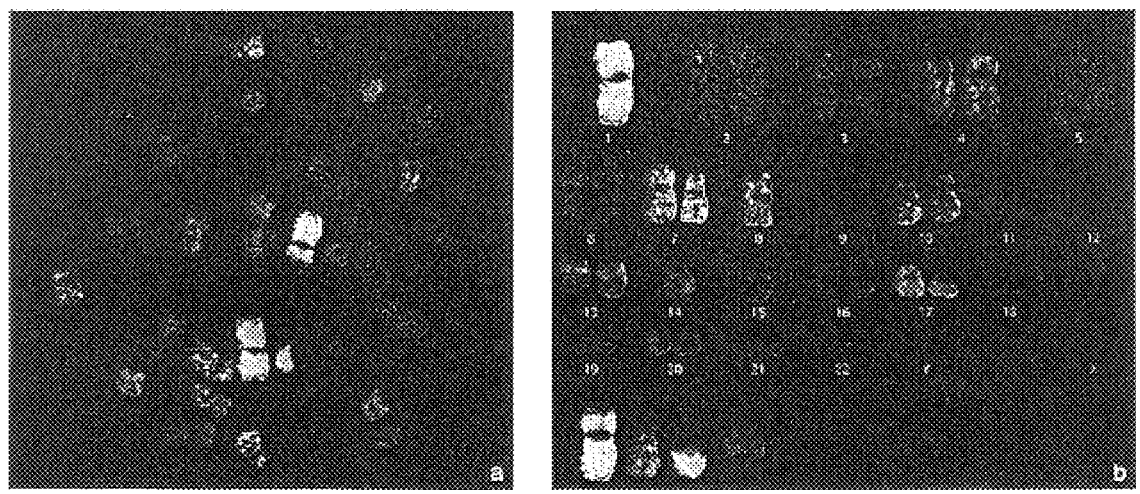

(a) Image (12 colours) resulting from the three primary dyes used for ratio labelling;
(b) Image of the binary (fourth) label (fluorescein, but shown in blue false colour);
(c) Thresholded image (b) to indentify the fluorescein positive and negative sets of chromosomes; Note: DEAC is used as direct probe label here (through ULS), whereas in FIG. 2, 3 and 4 is was used as binary label (as immunoconjugate).

Figure 6:
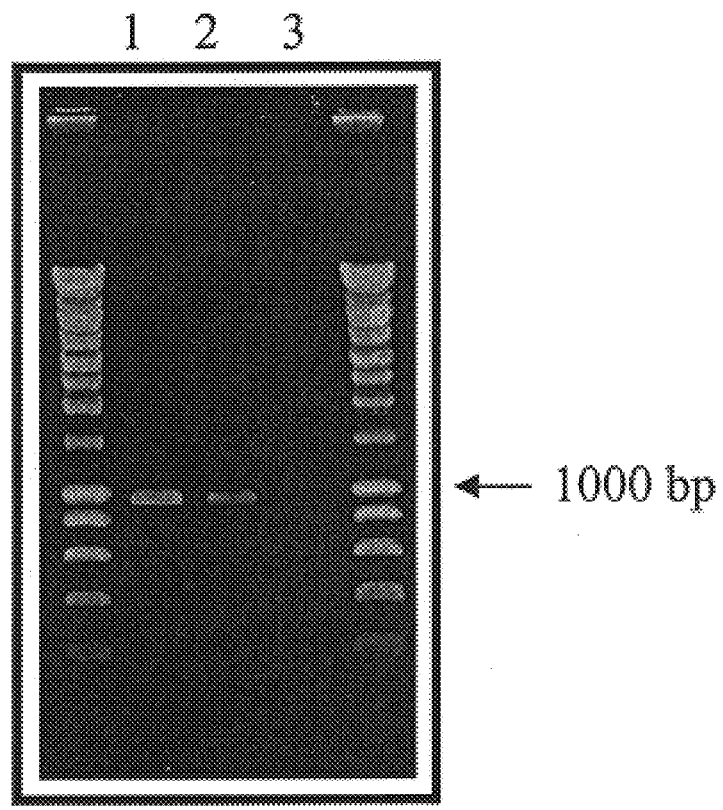

FIG. 6: Blocking of PCR with internal trans-ULS labelled oligonucleotides. PCR of a DNA fragment with a forward and reverse primer (lane 1) was inhibited by pre-hybridisation of the target DNA with a pool of 4 internal oligonucleotides (lane 2) and completely blocked if the internal oligonucleotides were labelled with trans-ULS (lane 3).

Figure 7:
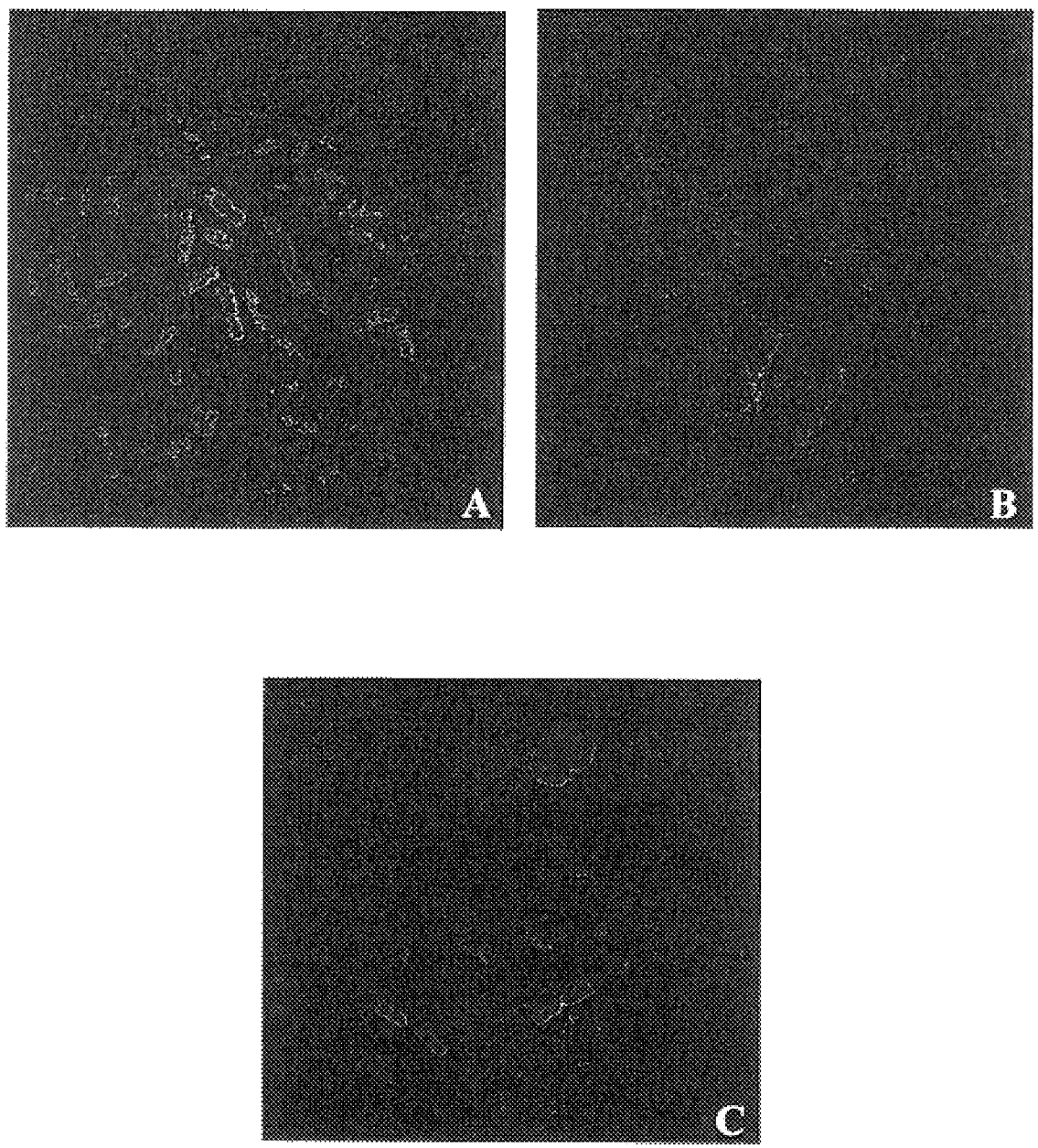

FIG. 7: FISH with repeat free human chromosome 1 specific probe. FIG. 7A shows FISH image of a human metaphase spread probe with human chromosome 1 probe. No use was made of human $C_o t$ 1 DNA. Note the high degree of non specific staining of other chromosomes present in the complement of the human genome which makes identification of chromosome 1 difficult. Reduced non specific cross-hybridisation of repetitive sequences present in the chromosome 1 specific probe was obtained by preannealing the probe with a 5 fold excess of human $C_o t$ 1 DNA (1 hour at 37° C.). Chromosome 1 could be identified with ease (FIG. 7B). The Chromosome 1 specific painting probe deprived from highly repetitive sequences through the use of trans-ULS allowed unambiguous identification of chromosome 1, without the use of human $C_o t$ 1 DNA, among the other chromosomes present in the complement of the human genome (FIG. 7C).

Figure 8:
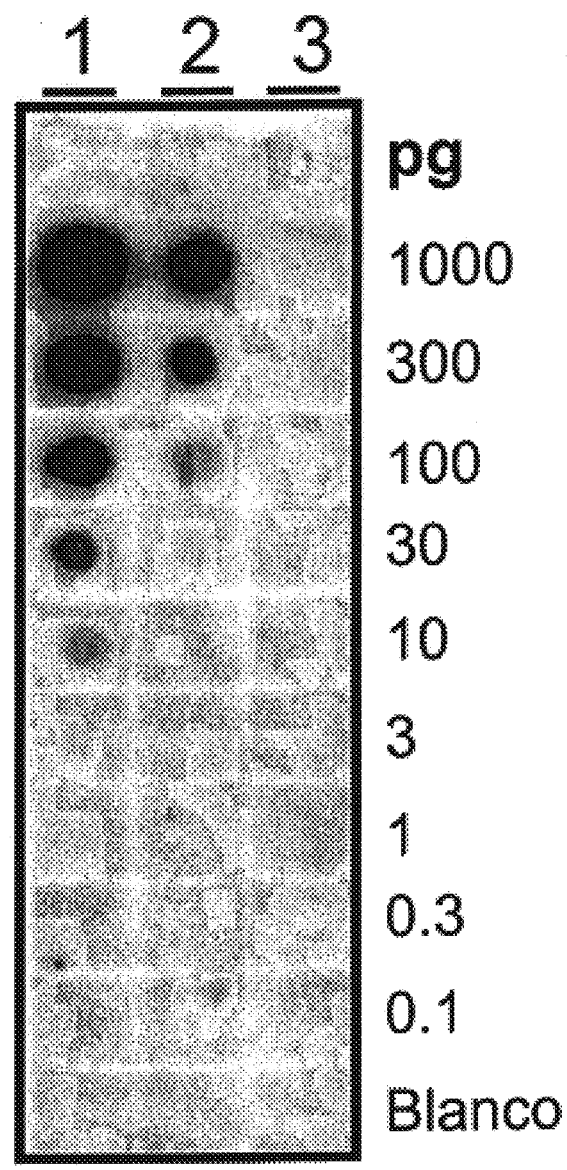

FIG. 8: Filter hybridisation analysis of HPV18 deprived homologous sequences in a HPV45 probe using the trans-ULS technology. Biotin end-labelled and trans-ULS labelled sonicated HPV18 DNA is pre-associated with DIG-ULS labelled HPV45 DNA. Biotin labelled HPV18–HPV45 hybrids are subsequently removed from the probe mixture using streptavidin magnetic beads. Detection of hybridisation is done using αDIG-AP antibodies in combination with CDP-Star™.

Lane 1, hybridisation of a DIG-ULS labelled HPV45 probe, pre-associated with non-labelled sonicated HPV18 DNA on spotted genomic HPV45;
Lane 2, hybridisation of a DIG-ULS labelled HPV45 probe, pre-associated with Biotin end-labelled and trans-ULS labelled HPV18 on spotted genomic HPV45;
Lane 3, hybridisation of a DIG-ULS labelled HPV45 probe, pre-associated with Biotin end-labelled and trans-ULS labelled HPV18, on spotted genomic HPV18.

Figure 9:
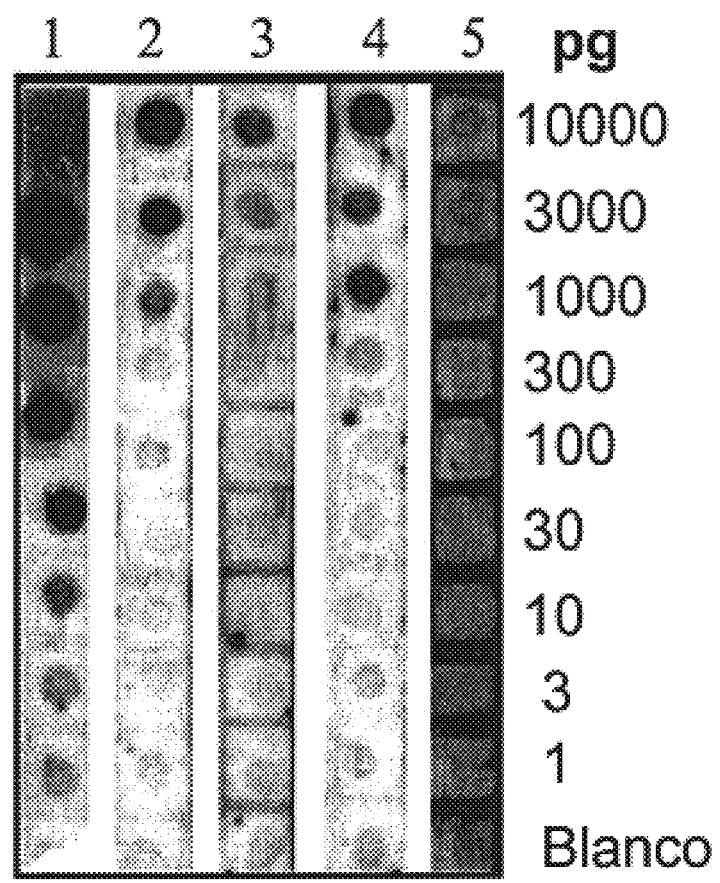

FIG. 9: Filter hybridisation analysis of an oligonucleotide mixture probes with biotinylated complementary oligonucleotides.

Lane 1, Biotin labelled complementary oligonucleotide mix hybridised on spotted oligonucleotides;
Lane 2, Biotin labelled complementary oligonucleotide mix pre-associated with a five fold excess of the oligonucleotides and hybridised on spotted oligonucleotides;
Lane 3, Biotin labelled complementary oligonucleotide mix pre-associated with a five fold excess of trans-ULS labelled oligonucleotides and hybridised on spotted oligonucleotides;
Lane 4, Biotin labelled complementary oligonucleotide mix pre-associated with a ten fold excess of the oligonucleotides and hybridised on spotted oligonucleotides;
Lane 5, Biotin labelled complementary oligonucleotide mix pre-associated with a ten fold excess of trans-ULS labelled oligonucleotides and hybridised on spotted oligonucleotides.

Figure 10:
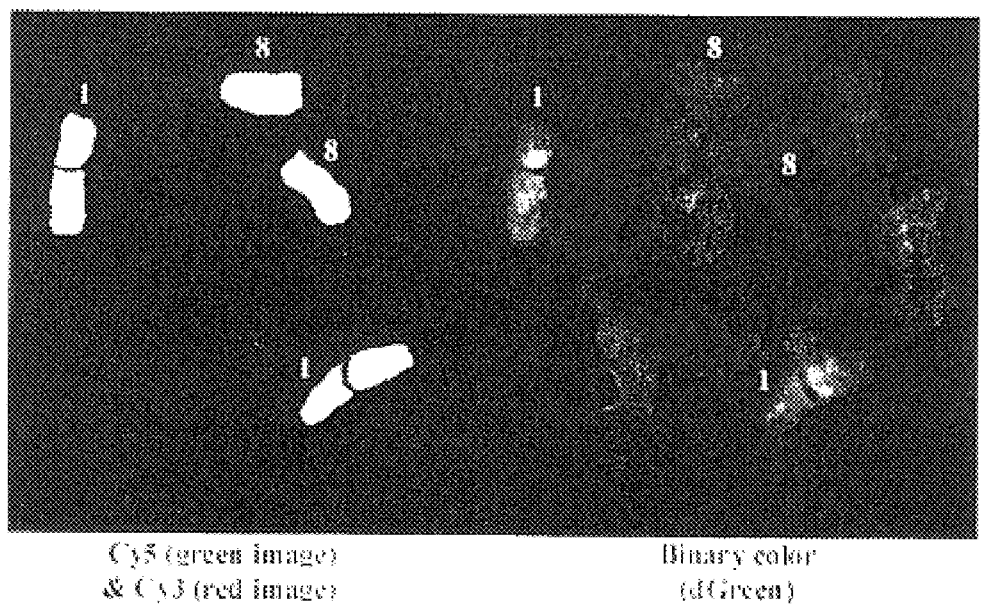

FIG. 10: COBRA with repeat free whole chromosome probes. Human chromosome paints specific for chromosome 1 and 8, depleted from repetitive sequences and COBRA labelled according to the invention, were probe onto human metaphase chromosome spreads. No use was made of human $C_o t$ 1 DNA. Chromosome 1 and 8 were ratio labelled with Cy3-ULS and Cy5-ULS whereas chromosome 1 was binary labelled only (dGREEN-ULS). Although the two chromosomes have the same ratio labels (Cy3 and Cy5) and ratio (50:50), the binary label made possible to discriminate the two chromosomes from each other.

REFERENCES

Schroeck et al., Science 273: 494–497, 1996
Speicher et al., Nature Genetics 12: 368–375, 1996
Nederlof et al., Cytometry 13: 839–845, 1992
Dauwerse et al., Hum Molec Genet 1: 593–598, 1992
Morrison and Legator, Cytometry 27: 314–326, 1997
Craig et al., Hum Genet 100: 472–476, 1997
Cohen et al., J. Am. Chem. Soc., 1980, Vol 102: 2487–2488
Eastman et al., Chem. Biol. Inter Act., 1988, Vol 67:71–80.
Pinto et al., Proc. Natl. Acad. Sci. USA, 1985, Vol 82:4616–4619.
Lepre et al., Biochemistry, 1987, Vol 26: 5651–5657.
Dalbies et al., Proc. Natl. Acad. Sci. USA, 1994, vol 91: 8147–8151.

TABLE 1 repetitive DNA test with trans-DDP ULS

| slide | Denat. 1 | repetitive DNA:ULS | Denat. (2) | Probe | FISH results |
|---|---|---|---|---|---|
| 1 | no | no | Yes | c#1-Flu | ++++ |
| 2 | yes | yes 1:0 | yes | c#1-Flu | ++ |
| 3 | yes | yes 1:0 | no | c#1-Flu | – |
| 4 | yes | yes 1:2 | no | c#1-Flu | ++ |
| 5 | yes | yes 1:2 | yes | c#1-Flu | ++ |
| 6 | yes | yes 1:1 | yes | c#1-Flu | +/– |
| 7 | yes | yes 2:1 | yes | c#1-Flu | + |
| 8 | yes | yes 4:1 | yes | c#1-Flu | ++ |
| 9 | yes | yes 8:1 | yes | c#1-Flu | ++ |

TABLE 2

| Chrom No. | µl DEAC ULS (26.7 µM) | µl Cy3 ULS (20 µM) | µl Cy5 ULS (13.3 µM) | ng probe DNA in hybrid. Mix |
|---|---|---|---|---|
| 1 | 30 | 0 | 0 | 500 |
| 2 | 0 | 0 | 30 | 300 |
| 3 | 0 | 30 | 0 | 400 |
| 4 | 30 | 0 | 0 | 500 |
| 5 | 0 | 0 | 30 | 600 |
| 6 | 0 | 30 | 0 | 500 |
| 7 | 22.5 | 9 | 0 | 300 |
| 8 | 22.5 | 0 | 9 | 400 |
| 9 | 0 | 22.5 | 7.5 | 500 |
| 10 | 22.5 | 9 | 0 | 500 |
| 11 | 7.5 | 0 | 22.5 | 500 |
| 12 | 0 | 22.5 | 7.5 | 400 |
| 13 | 22.5 | 0 | 9 | 300 |
| 14 | 19.5 | 0 | 15 | 300 |
| 15 | 0 | 18 | 15 | 300 |
| 16 | 15 | 18 | 0 | 300 |
| 17 | 19.5 | 0 | 15 | 300 |
| 18 | 0 | 18 | 15 | 400 |
| 19 | 7.5 | 22.5 | 0 | 400 |
| 20 | 7.5 | 0 | 22.5 | 400 |
| 21 | 0 | 10.5 | 22.5 | 300 |
| 22 | 7.5 | 22.5 | 0 | 400 |
| X | 0 | 10.5 | 22.5 | 400 |
| Y | 15 | 18 | 0 | 100 |

TABLE 3

| Row | Antibody | Av-Flu | Av-DNP | Av-Flu/DNP | | |
|---|---|---|---|---|---|---|
| 1 | AP anti-Flu | + | – | + | | |
| 2 | AP anti-DNP | – | + | + | | |
| 3 | AP anti-Flu AP anti-DNP | + | + | + | | |
| 4 | AP anti-DIG | – | – | – | | |

| | | BSA-Flu | BSA-DNP | BSA-Flu/DNP | BSA-DIG | BSA-Flu/DNP/DIG |
|---|---|---|---|---|---|---|
| 5 | AP anti-Flu | + | – | + | – | + |
| 6 | AP anti-DNP | – | + | + | – | + |
| 7 | AP anti-Flu AP anti-DNP | + | + | + | – | + |
| 8 | AP anti-DIG | – | – | – | + | + |
| 9 | AP anti-Flu AP anti-DNP AP anti-DIG | + | + | + | + | + |

What is claimed is:

1. A method for preventing hybridization of a repetitive chromosomal nucleic acid sequence, while permitting hybridization of a unique chromosomal nucleic acid sequence, the method comprising the steps of:

providing a nucleic acid sequence that is complementary to the repetitive sequence, wherein the complementary sequence or the repetitive sequence or both comprise a cross-linking agent, the cross-linking agent being capable of cross-linking the complementary sequence to the repetitive sequence when the complementary sequence is hybridized to the repetitive sequence; and hybridizing the repetitive nucleic acid sequence to its complementary sequence in the presence of the unique sequence, thereby cross-linking the complementary sequence to the repetitive sequence;

whereby the cross-linked repetitive sequence is prevented from further hybridizing, while the unique sequence is permitted to hybridize.

2. The method according to claim 1, wherein the complementary nucleic acid sequence is DNA, RNA or PNA.

3. The method according to claim 1, wherein the repetitive nucleic acid sequence is DNA.

4. The method according to claim 1, wherein at least two repetitive nucleic acid sequences are hybridized to complementary sequences comprising cross-linking agents.

5. The method according to claim 1, wherein the cross-linking agent comprises a transition metal.

6. The method according to claim 1, wherein the transition metal is platinum.

7. The method according to claim 1, wherein the cross-linking agent is (trans)-dichlorodiammineplatinum.

8. A method for preventing hybridization of a repetitive chromosomal nucleic acid sequence, while permitting hybridization of a unique chromosomal nucleic acid sequence, the method comprising the steps of:

providing a nucleic acid sequence that is complementary to the repetitive sequence and that comprises a cross-linking agent capable of cross-linking the complementary sequence to the repetitive sequence when the complementary sequence is hybridized to the repetitive sequence; and hybridizing the repetitive nucleic acid sequence to its complementary sequence in the presence of the unique sequence, thereby cross-linking the complementary sequence to the repetitive sequence;

whereby the cross-linked repetitive sequence is prevented from further hybridizing, while the unique sequence is permitted to hybridize.

9. The method according to claim 8, wherein the complementary nucleic acid sequence is DNA, RNA, or PNA.

10. The method according to claim 8, wherein the repetitive nucleic acid sequence is DNA.

11. The method according to claim 8, wherein at least two repetitive nucleic acid sequences are hybridized to complementary sequences.

12. The method according to claim 8, wherein the cross-linking agent comprises a transition metal.

13. The method according to claim 8, wherein the transition metal is platinum.

14. The method according to claim 8, wherein the cross-linking agent is (trans)-dichlorodiammineplatinum.

15. A method for increasing the number of a single stranded unique chromosomal DNA sequence relative to the number of a single stranded repetitive chromosomal DNA sequence, the method comprising the steps of:

providing a nucleic acid sequence that is complementary to the repetitive DNA sequence, wherein the complementary sequence or the repetitive DNA sequence or both comprise a cross-linking agent, the cross-linking agent capable of cross-linking the complementary sequence to the repetitive DNA sequence when the complementary sequence is hybridized to the repetitive DNA sequence; and hybridizing the repetitive DNA sequence to its complementary sequence in the presence of the unique DNA sequence, thereby cross-linking the complementary sequence to the repetitive DNA sequence;

whereby the cross-linked repetitive DNA sequence is prevented from further hybridizing and/or replicating, and the number of the single stranded unique DNA sequence relative to the number of the single stranded repetitive DNA sequence is increased.

16. The method according to claim 15, wherein the complementary sequence is DNA, RNA, or PNA.

17. The method according to claim 15, wherein at least two repetitive sequences are hybridized to complementary sequences comprising cross-linking agents.

18. The method according to claim 15, wherein the cross-linking agent comprises a transition metal.

19. The method according to claim 15, wherein the transition metal is platinum.

20. The method according to claim 15, wherein the cross-linking agent is (trans)-dichlorodiammineplatinum.

21. A method for selectively replicating a unique chromosomal nucleic acid sequence in the presence of a repetitive chromosomal nucleic acid sequence, the method comprising the steps of:

providing a nucleic acid sequence that is complementary to the repetitive sequence and that comprises a cross-linking agent capable of cross-linking the complementary sequence to the repetitive sequence when the complementary sequence is hybridized to the repetitive sequence;

hybridizing the repetitive nucleic acid sequence to its complementary sequence, thereby cross-linking the complementary sequence to the repetitive sequence; and selectively replicating the unique sequence in the presence of the repetitive sequence cross-linked to its complementary sequence.

22. The method according to claim 21, wherein the complementary sequence is DNA, RNA, or PNA.

23. The method according to claim 21, wherein the repetitive sequence is DNA.

24. The method according to claim 21, wherein at least two repetitive sequences are hybridized to complementary sequences.

25. The method according to claim 21, wherein the cross-linking agent comprises a transition metal.

26. The method according to claim 21, wherein the transition metal is platinum.

27. The method according to claim 21, wherein the cross-linking agent is (trans)-dichlorodiammineplatinum.

28. A method for preparing probes suitable for detecting unique sequences of a target chromosome, the chromosome comprising unique DNA sequences and repetitive DNA sequences, the method comprising the steps of:

providing fragments of the chromosome;

providing nucleic acid sequences that are complementary to the repetitive DNA sequences, wherein the complementary sequences or the repetitive DNA sequences or both comprise a cross-linking agent, the cross-linking agent capable of cross-linking the complementary sequences to the repetitive DNA sequences when the complementary sequences are hybridized to the repetitive DNA sequences;

hybridizing the repetitive DNA sequences to the complementary sequences in the presence of the unique DNA sequences, thereby cross-linking the complementary sequences to the repetitive DNA sequences, whereby the cross-linked repetitive DNA sequences are prevented from further hybridizing; and labeling the unique DNA sequences; wherein the labeled, unique DNA sequences are suitable for detecting unique DNA sequences of the target chromosome.

29. The method according to claim 28, further comprising replicating the unique DNA sequences after the repetitive DNA sequences have been cross-linked to the complementary sequences.

30. The method according to claim 28, wherein the complem entary sequence is DNA, RNA, or PNA.

31. The method according to claim 28, wherein the cross-inking agent comprises a transition metal.

32. The method according to claim 31, wherein the transition metal is platinum.

33. The method according to claim 28, wherein the cross-linking agent is (trans)-dichlorodiammineplatinum.

34. The method according to claim 28, wherein the nucleic acid sequences complementary to the repetitive DNA sequences are fragments of a chromosome other than the target chromosome.

35. The method according to claim 28, wherein the nucleicacid sequences complementary to the repetitive DNA sequences comprise the cross-linking agent.

36. Probes suitable for detecting unique sequences of a target chromosome prepared in accordance with claim 28.

37. Probes according to claim 36, wherein the cross-linking agent comprises a transition metal.

38. Probes according to claim 37, wherein the transition metal is platinum.

39. Probes according to claim 38, wherein the cross-linking agent is (trans)-dichlorodiarnuineplatinum.

* * * * *

UNITED STATES PATENT AND TRADEMARK OFFICE
CERTIFICATE OF CORRECTION

PATENT NO. : 6,406,850 B2
DATED : June 18, 2002
INVENTOR(S) : Volkers et al.

It is certified that error appears in the above-identified patent and that said Letters Patent is hereby corrected as shown below:

Title page,
Item [74], now reads "Hoffman & Baron, LLP" should read -- Hoffmann & Baron, LLP --

Column 5,
Line 33, now reads "(MRNA)" should read -- (mRNA) --.

Column 11,
Line 16, now reads "10$\mu$M Tris.HCl pH 8.5." should read -- 10mM Tris.HCl pH 8.5. --
Line 48, after "$C_0$tl-DNA." the following section should be inserted:
-- After a 10 min post-hybridisation wash in 2xSSC/0.1% Tween 20 at 37°C to remove coverslips, the slides were washed 2 x 5 min in 50% formamide, 2XSSC, pH 7 at 44°C. This was followed by 2 washed (5 min each) in 0.1xSSC at 60°C and a 5 min wash at RT in TNT (0.1M Tris.HCl pH 7.4, 0.15 M NaCl, 0.05% Tween 20). The DIG-ULS labelled probes were detected with a mouse monoclonal antibody against digoxin (Sigma) followed by a rabbit anti mouse antibody conjugated to FITC (Sigma). Chromosomes were counterstained with DAPI. The slides were --
Line 61, the following paragraph should be inserted:
-- Image acquisition and analysis was performed on a Cytovision workstation (Applied Imaging, Sunderland, UK). This system consists of a PC (Pentium 133MHz processor, 24Mb Ram, 2.1 Gb disc and 17" display) interfaced to a Coolview camera (Photonic Science). The camera has thermo-electric cooling, which allows on chip integration up to circa 30 seconds. Images are digitised in an 8-bit 768 x 512 image format. --

Column 15,
Line 3, now reads "Cotl DNA." should read -- $C_0$t1 DNA. --
Lines 32-44, should read -- In this example we in essence repeated the experiments described in example 2. Human Papllomavirus (HPV) type 16 primers HPVfor (SEQ ID NO.:1) and HPVrev (SEQ ID NO.: 2) yielded a fragment of 945 bp in a polymerase chain reaction (PCR). Four internal primers were designed: primer TU16for1 (SEQ ID NO.: 3), primer TU16for2 (SEQ ID NO.: 4), primer TU16rev1 (SEQ ID NO.: 5), and primer TU16rev2 (SEQ ID NO.: 6). --
Line 15, now reads "50 pg" should read -- 50 $\mu$g --

UNITED STATES PATENT AND TRADEMARK OFFICE
CERTIFICATE OF CORRECTION

PATENT NO.   : 6,406,850 B2
DATED        : June 18, 2002
INVENTOR(S)  : Volkers et al.

It is certified that error appears in the above-identified patent and that said Letters Patent is hereby corrected as shown below:

Column 19,
Line 25, now reads "370°C." should read -- 37°C. --

Column 22,
Line 46, now reads "protein solution with 50 pl" should read -- protein solution with 50 $\mu$l --

Column 23,
Line 4, now reads "NBT/SCIP" should read -- NBT/BCIP --

Signed and Sealed this

Eleventh Day of February, 2003

JAMES E. ROGAN
*Director of the United States Patent and Trademark Office*

SEQUENCE LISTING

<160> NUMBER OF SEQ ID NOS: 6

<210> SEQ ID NO 1
<211> LENGTH: 20

-continued

```
<212> TYPE: DNA
<213> ORGANISM: Human Papillomavirus

<400> SEQUENCE: 1
tcaaaagcca ctgtgtcctg                                           20

<210> SEQ ID NO 2
<211> LENGTH: 18
<212> TYPE: DNA
<213> ORGANISM: Human Papillomavirus

<400> SEQUENCE: 2 aaccacccccc acttccac                                            18

<210> SEQ ID NO 3
<211> LENGTH: 32
<212> TYPE: DNA
<213> ORGANISM: Human Papillomavirus

<400> SEQUENCE: 3
agagctgcaa aaggagatt atttgaaagc ga                              32

<210> SEQ ID NO 4
<211> LENGTH: 30
<212> TYPE: DNA
<213> ORGANISM: Human Papillomavirus

<400> SEQUENCE: 4
agagacaact gatctctact gttatgagca                                30

<210> SEQ ID NO 5
<211> LENGTH: 30
<212> TYPE: DNA
<213> ORGANISM: Human Papillomavirus

<400> SEQUENCE: 5
tcctgtgcag taaacaacgc atgtgctgtc                                30

<210> SEQ ID NO 6
<211> LENGTH: 37
<212> TYPE: DNA
<213> ORGANISM: Human Papillomavirus

<400> SEQUENCE: 6
cgtgtgtgct ttgtacgcca caaccgaagc gtagagt                        37
```